(12) United States Patent
Brandao et al.

(10) Patent No.: US 10,682,062 B2
(45) Date of Patent: *Jun. 16, 2020

(54) ANIMAL TAG SYSTEM

(71) Applicant: Herddogg, Inc., Ashand, OR (US)

(72) Inventors: Melissa Brandao, Ashland, OR (US); David W. Proctor, Emerald Hills, CA (US)

(73) Assignee: Herddogg, Inc., Longmont, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/196,606

(22) Filed: Nov. 20, 2018

(65) Prior Publication Data

US 2019/0090754 A1 Mar. 28, 2019

Related U.S. Application Data

(63) Continuation of application No. 15/850,326, filed on Dec. 21, 2017, now Pat. No. 10,130,265, which is a
(Continued)

(51) Int. Cl.
*A61B 5/01* (2006.01)
*A01K 11/00* (2006.01)
(Continued)

(52) U.S. Cl.
CPC ............ *A61B 5/015* (2013.01); *A01K 11/004* (2013.01); *A01K 11/006* (2013.01);
(Continued)

(58) Field of Classification Search
CPC .... A61B 5/015; A01K 11/004; A01K 29/005; A01K 11/006; A01K 15/023
(Continued)

(56) References Cited

U.S. PATENT DOCUMENTS 4,262,632 A 4/1981 Hanton et al.
4,635,587 A 1/1987 Leonardo
(Continued)

FOREIGN PATENT DOCUMENTS

KR 100926577 B1 11/2009
KR 20100064152 6/2010
(Continued)

*Primary Examiner* — John A Tweel, Jr.
(74) *Attorney, Agent, or Firm* — Hall Estill Attorneys at Law

(57) ABSTRACT

Apparatus for managing animals such as but not limited to livestock. In some embodiments, a tag assembly is configured for attachment to an outer ear of an animal. The tag assembly has a main body and a shaft that extends through an aperture extending through the outer ear to attach the main body to a facing surface of the outer ear. A primary temperature sensor of the tag assembly is configured to obtain outer ear temperature data indicative of an outer ear temperature of the outer ear. A control circuit is configured to receive the outer ear temperature data via a wireless communication link with the tag assembly. The control circuit determines a health state of the animal in response to a localized change in a magnitude of the outer ear temperature data in relation to a set of ambient temperature data over a selected time interval.

20 Claims, 18 Drawing Sheets

Related U.S. Application Data continuation-in-part of application No. 15/595,561, filed on May 15, 2017, now Pat. No. 9,848,577.

(51) Int. Cl.
| | |
|---|---|
| *A01K 29/00* | (2006.01) |
| *A61D 17/00* | (2006.01) |
| *A61B 5/00* | (2006.01) |
| *A01K 15/02* | (2006.01) |
| *G16H 10/60* | (2018.01) |
| *A61B 5/0205* | (2006.01) |
| *A61B 5/024* | (2006.01) |
| *A61B 5/11* | (2006.01) |
| *A61B 5/145* | (2006.01) |
| *A61B 5/02* | (2006.01) |
| *G16H 40/67* | (2018.01) |
| *G16H 50/20* | (2018.01) |

(52) U.S. Cl.
CPC .......... *A01K 15/023* (2013.01); *A01K 29/005* (2013.01); *A61B 5/01* (2013.01); *A61B 5/6816* (2013.01); *A61D 17/002* (2013.01); *A61D 17/006* (2013.01); *A61B 5/0024* (2013.01); *A61B 5/024* (2013.01); *A61B 5/02028* (2013.01); *A61B 5/02055* (2013.01); *A61B 5/1112* (2013.01); *A61B 5/1118* (2013.01); *A61B 5/14542* (2013.01); *A61B 2503/40* (2013.01); *A61B 2562/029* (2013.01); *A61B 2562/0219* (2013.01); *A61B 2562/0233* (2013.01); *A61B 2562/0257* (2013.01); *A61B 2562/0271* (2013.01); *G16H 10/60* (2018.01); *G16H 40/67* (2018.01); *G16H 50/20* (2018.01)

(58) Field of Classification Search
USPC ...................................................... 340/573.3
See application file for complete search history.

(56) References Cited

U.S. PATENT DOCUMENTS

| | | |
|---|---|---|
| 5,984,875 A | 11/1999 | Brune |
| 6,059,733 A | 5/2000 | Brune et al. |
| 6,113,539 A | 9/2000 | Ridenour |
| 6,318,289 B1 | 11/2001 | Pratt |
| 6,569,092 B1 | 5/2003 | Guichon et al. |
| 6,773,405 B2 | 8/2004 | Fraden et al. |
| 6,847,892 B2 | 1/2005 | Zhou et al. |
| 7,026,939 B2 | 4/2006 | Letkomiller et al. |
| 7,110,372 B2 | 9/2006 | Kovacs et al. |
| 7,196,628 B2 | 3/2007 | Hixson |
| 7,467,603 B2 | 12/2008 | Davies |
| 7,705,736 B1 | 4/2010 | Kedziora |
| 7,843,350 B2 | 11/2010 | Geissler et al. |
| 7,868,769 B2 | 1/2011 | March et al. |
| 8,663,106 B2 | 3/2014 | Stivonic et al. |
| 8,708,926 B2 | 4/2014 | Grassi et al. |
| 8,979,757 B2 | 3/2015 | Mottram et al. |
| 9,370,170 B2 | 6/2016 | Downing et al. |
| 9,848,577 B1 | 12/2017 | Brandao |
| 10,130,265 B1 * | 11/2018 | Brandao .............. A01K 11/006 |
| 2002/0010390 A1 | 1/2002 | Guice et al. |
| 2004/0233971 A1 | 11/2004 | Meads et al. |
| 2005/0145187 A1 | 7/2005 | Gray |
| 2008/0314325 A1 | 12/2008 | Hempstead et al. |
| 2010/0030036 A1 | 2/2010 | Brune |
| 2011/0251514 A1 | 10/2011 | Fults et al. |
| 2013/0197323 A1 | 8/2013 | Rettedal et al. |
| 2016/0120628 A1 | 5/2016 | Kapil |
| 2017/0156288 A1 | 6/2017 | Singh |
| 2017/0224456 A1 | 8/2017 | Hilpert et al. |

FOREIGN PATENT DOCUMENTS

| | | |
|---|---|---|
| WO | 2014/081072 A1 | 5/2014 |
| WO | 2015/164845 A1 | 10/2015 |
| WO | 2016/037190 A1 | 3/2016 |
| WO | 2016037190 A1 | 3/2016 |

* cited by examiner

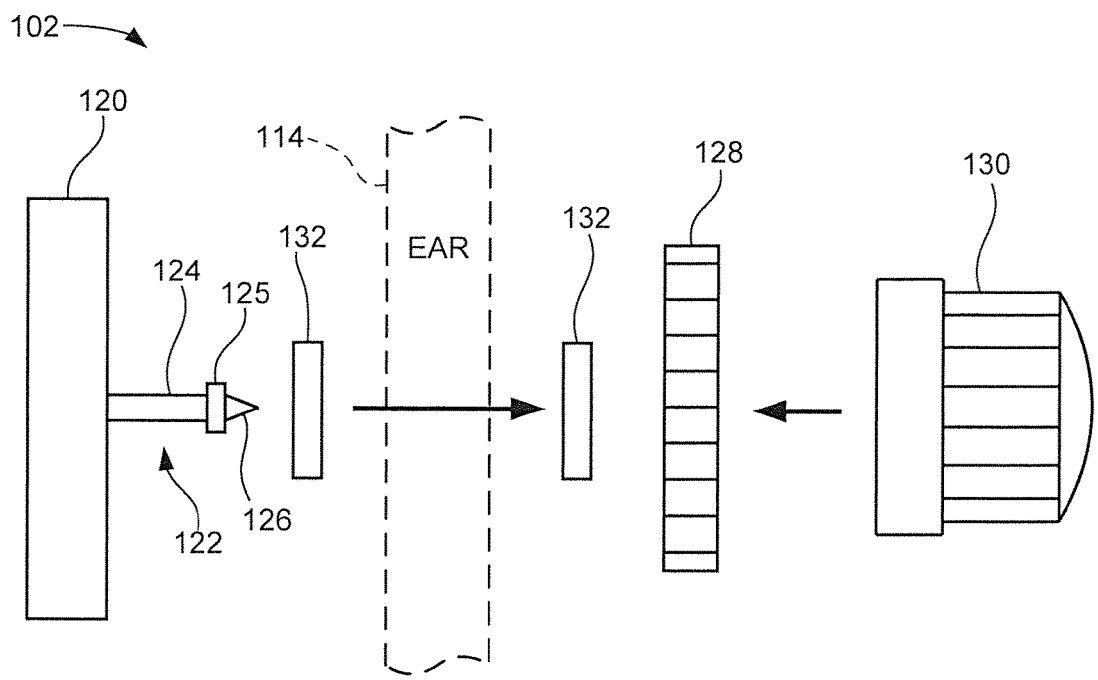
FIG. 3A
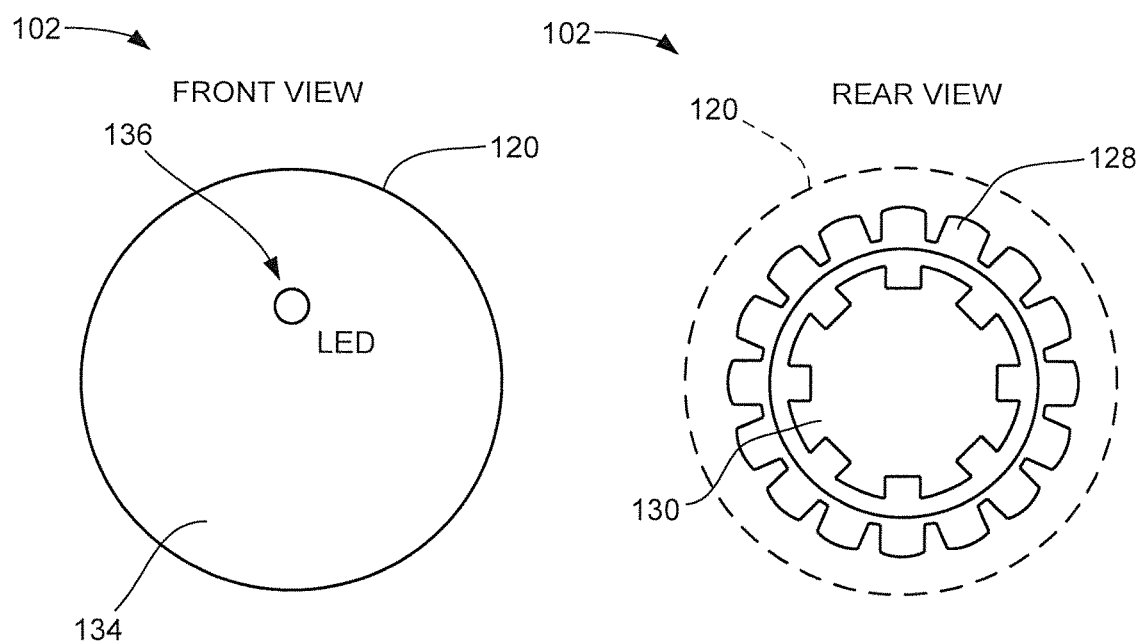
FIG. 3B
FIG. 3C

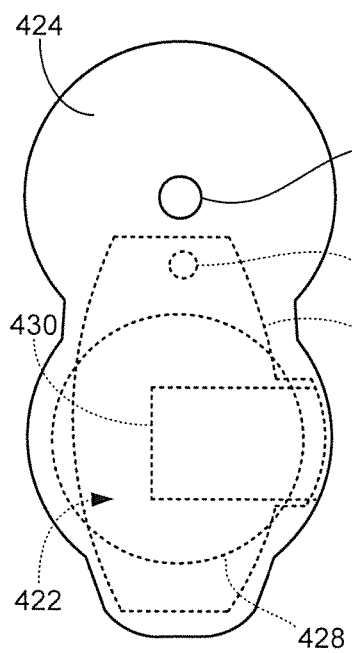
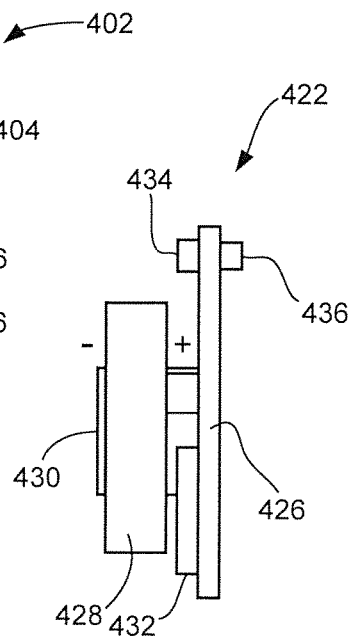
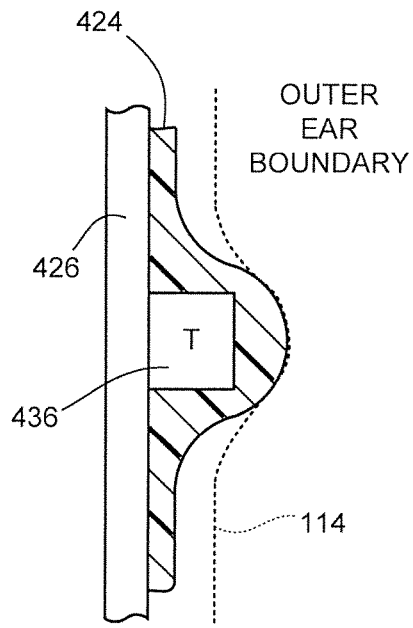
FIG. 27　　　FIG. 28　　　FIG. 29
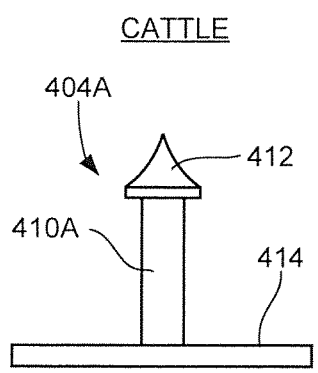
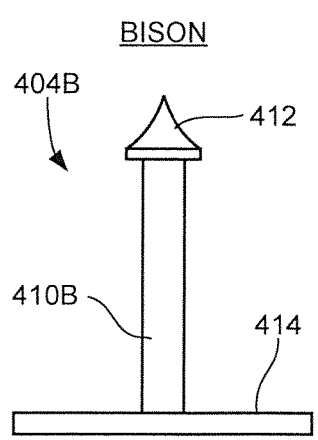
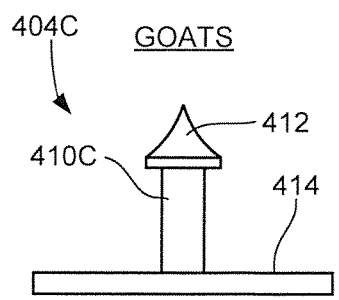
FIG. 30A　　　FIG. 30B　　　FIG. 30C

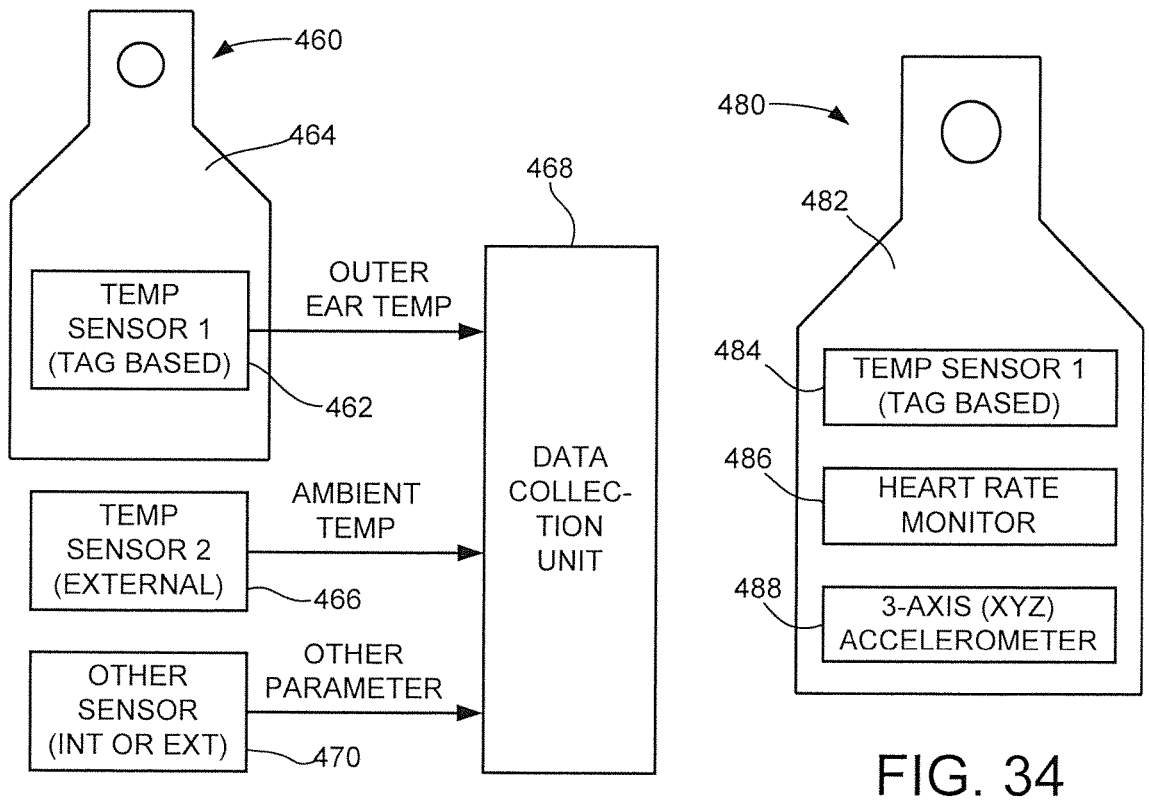
FIG. 33
FIG. 34
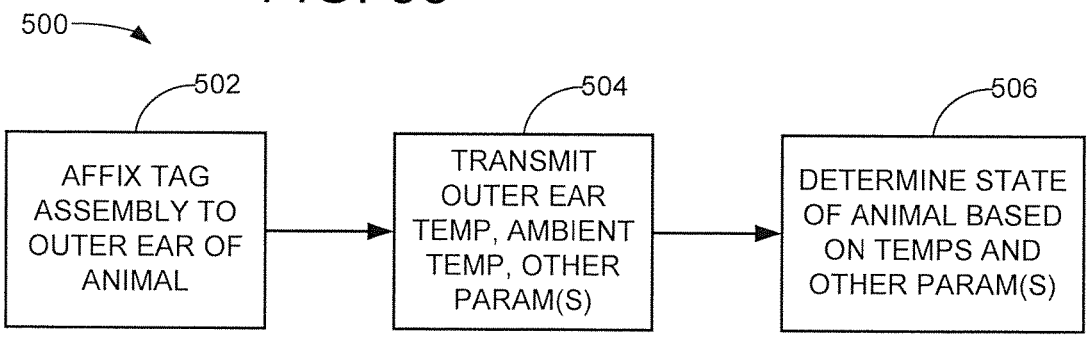
FIG. 35
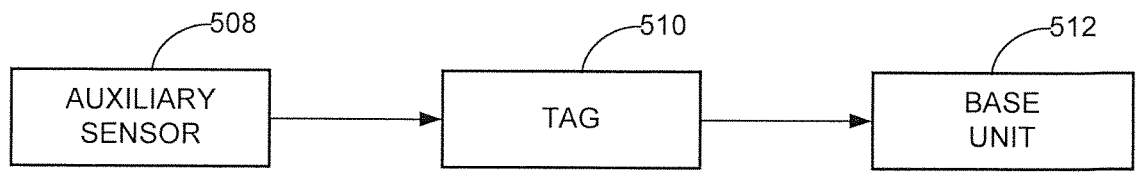
FIG. 36

ANIMAL TAG SYSTEM

RELATED APPLICATIONS

The present application is a continuation of U.S. patent application Ser. No. 15/850,326 filed Dec. 21, 2017, now issued as U.S. Pat. No. 10,130,265 on Nov. 20, 2018 which is a continuation-in-part (CIP) of U.S. patent application Ser. No. 15/595,561 filed May 15, 2017, now U.S. Pat. No. 9,848,577 which issued on Dec. 26, 2017.

BACKGROUND

Livestock management is generally concerned with the care and maintenance of livestock (e.g., domesticated animals such as cattle, sheep, swine, etc.) in an agricultural setting. Livestock management systems are usually implemented with a view toward the commercial production of commodities from such animals for human consumption and use.

Modern agricultural practices have increasingly incorporated the use of technology to assist in livestock management efforts. It is common for domesticated livestock animals such as cattle to wear or otherwise carry machine interactive tags that can be used to track the location and status of the individual animals in a particular setting, such as a dairy farm, feed lot, ranch, etc.

Data collection and analysis systems can aggregate tag data to enable a user to perform various livestock management tasks. Temperature data obtained from a particular tag may be used to indicate the health status of the animal. Location data obtained from a tag may facilitate other animal welfare activities such as milking operations, vaccinations, search and rescue efforts for lost animals, etc.

While existing technical solutions in the area of livestock management have been found operable, there remains a continued need for improvements in the art, and it is to these and other improvements that various embodiments of the present disclosure are directed.

SUMMARY

Various embodiments are generally directed to an apparatus for managing animals such as but not limited to livestock.

In some embodiments, a tag assembly is configured for attachment to an outer ear of an animal. The tag assembly has a main body and a shaft that extends through an aperture extending through the outer ear to attach the main body to a facing surface of the outer ear. A primary temperature sensor of the tag assembly is configured to obtain outer ear temperature data indicative of an outer ear temperature of the outer ear. A control circuit is configured to receive the outer ear temperature data via a wireless communication link with the tag assembly. The control circuit determines a health state of the animal in response to a localized change in a magnitude of the outer ear temperature data in relation to a set of ambient temperature data over a selected time interval.

These and other features and advantages of the various embodiments can be understood from a review of the following detailed description and the accompanying drawings.

BRIEF DESCRIPTION OF DRAWINGS

FIG. 3A is an exploded side-elevational representation of the tag assembly of FIG. 2 in some embodiments.

FIG. 3B is a front facing view of the assembled tag from FIG. 3A.

FIG. 3C is a rear facing view of the assembled tag from FIG. 3A.

FIG. 27 is another rear facing view of the tag assembly to represent certain internal elements of interest including a battery, a printed circuit board (PCB) and various sensors.

FIG. 28 is a side-view representation of the internal elements of FIG. 27.

FIG. 29 shows the temperature sensor with an overmolded bump to provide operative contact with the outer ear of the animal from FIG. 24.

FIGS. 30A, 30B and 30C show different connection members suitable for different types of animals.

FIG. 33 shows another schematic depiction of a tag assembly in which an external ambient temperature measurement is provided to a control circuit.

FIG. 34 shows another schematic depiction of yet another tag assembly including additional sensors such as a heart rate monitor and a three (3) axis accelerometer.

FIG. 35 is a sequence diagram to illustrate usage of the various tag assemblies disclosed herein in accordance with some embodiments.

FIG. 36 shows the use of a separate auxiliary tag which communicates with another tag assembly in further embodiments.

DETAILED DESCRIPTION

Figure 1:
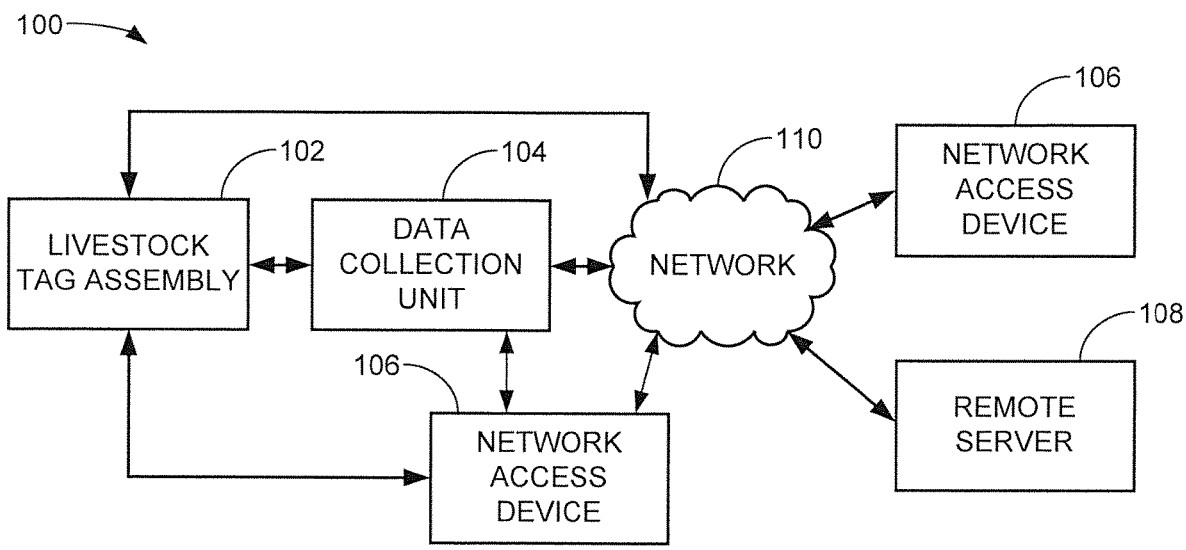
FIG. 1 is a functional block diagram for a livestock management system constructed and operated in accordance with various embodiments.

The present disclosure is generally directed to an animal management system useful for managing various types of animals. Various embodiments discussed in detail herein are generally directed to systems for managing livestock, such as but not limited to cattle, in an agricultural setting. The systems, methods and devices set forth herein are not so limited, however, as other forms domesticated and wild mammals may be managed using these techniques, including but not limited to wolves, large cats, deer, bison, goats, elephants, etc. Moreover, it will be immediately apparent that the various techniques disclosed herein can be applied to other forms of animals, including humans.

As explained below, some embodiments provide a tag assembly adapted to collect, receive and transmit data associated with a livestock animal, such as a cow. The tag assembly has a tag (base) which encloses various electronic components. An elongated shaft assembly extends from the tag to pierce and extend through the ear of an animal. A backing member is attachable to the distal end of the shaft assembly to retain the tag assembly to the ear.

A first temperature sensor is incorporated into the tag assembly. The first temperature sensor may be disposed within a medial portion of the shaft assembly to obtain a first sequence of temperature measurements indicative of an external ear temperature of the animal (e.g., a temperature of the auricle, or outer ear of the animal, also referred to herein as an outer ear temperature of the animal). Other locations for the first temperature sensor may be used, including along a facing surface of the tag assembly to press against or otherwise contactingly abut an outer surface of the outer ear to obtain the outer ear temperature of the animal.

A second temperature sensor is also provided. In some cases, the second temperature sensor is disposed within the tag to provide a second sequence of temperature measurements indicative of an ambient temperature of an environment external to the animal. In other cases, the second temperature sensor is disposed external to the tag assembly, such as in a nearby data collection unit, from a different tag assembly on another animal, etc. to obtain the ambient temperature measurements. Correlation of the first and second temperature sequences can be carried out to ascertain a state of the animal. A number of additional sensors of various types may further provide information regarding the state of the animal.

In some cases, a permanent tag configuration is used so that the backing member can be removed and replaced on a regularly scheduled basis. The removable backing member may house a battery or other power source, as well as one or more peripheral devices such as additional circuits, energy collection devices, etc. In other cases, a one-time use tag configuration is used so that the backing member permanently connects to the distal end of the shaft. In this case, the battery or other power source may be disposed within the tag rather than in the backing member, although such is not required. In still other cases, a lifetime tag can be used that is secured using a connection member that can be cut or otherwise removed to allow the tag to be installed on a new, different animal.

A variety of different control circuits, sensors and communication circuits can be incorporated into the tag and/or backing member to carry out various functions. The tag assembly can be configured to interface with various communication devices locally and/or over one or more networks, including other nearby tag assemblies, data collection units, network access devices and remote servers. Data collected from the tag assembly can be analyzed to further various livestock management efforts.

These and other features of various embodiments will now be understood beginning with a review of FIG. 1 which provides a functional block representation of a livestock management system 100.

The system 100 includes a number of different modular components that can be utilized within the system as desired under different operational environments. Representative components include a livestock tag assembly 102, a data collection unit 104, a number of network access devices 106 and a remote server 108. These components can be configured to communicate with either other as required, either directly or via one or more networks 110 (including a local wireless network, the Internet, etc.). The construction and interaction of these various components will be discussed in detail below.

Figure 2:
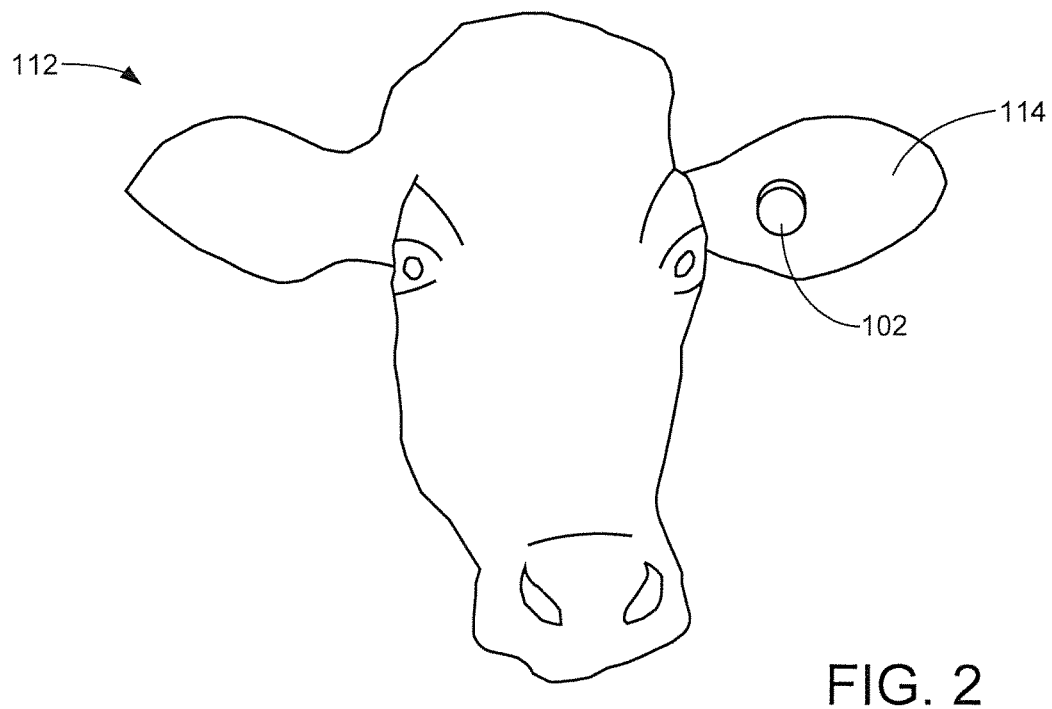
FIG. 2 is a schematic depiction of a cow having a tag assembly of the system of FIG. 1 in accordance with some embodiments.

FIG. 2 depicts the head of a livestock animal 112 (in this case, a cow) to illustrate an exemplary placement of the tag assembly 102 in a centered relation to an ear 114 of the cow. As noted above, while the various embodiments presented herein are particularly suitable for the management of a herd of cattle, the system can be readily adapted for use with substantially any type and/or group of animal, including domesticated or wild mammals.

FIG. 3A is an exploded representation of the tag assembly 102 of FIGS. 1-2 in accordance with some embodiments. Other configurations can be used so the arrangement of FIG. 3A is merely exemplary and is not limiting. The tag assembly 102 includes a tag 120, also referred to as a tag member, a base member, a base and/or a first attachment member. The tag 120 is substantially disc-shaped and may be on the order of about 2 inches, in. in diameter by about ¼ in. in thickness. Other sizes and shapes may be used. The tag 120 has an outer housing that is formed of injection molded plastic or other environmentally suitable material. The housing provides an interior sealed environment for various circuit components used by the tag assembly.

A shaft assembly 122 extends from a central portion of the tag 120. The shaft assembly 122 includes an elongated shaft 124 that is cylindrically shaped and which terminates with a radially-extending retention flange 125. The flange 125 is disc-shaped and has a larger diameter than the shaft 124 to serve as a retention feature. The shaft 124 and flange 125 are hollow to form a central passageway therethrough and may be made of the same material as the tag 120.

The shaft assembly 122 terminates at a distal end thereof with a conically shaped tip 126. The tip 126 is electrically conductive and may be made of metal or other material to facilitate piercing of the ear 114 during installation as well as conduction of electricity from a power source during operation.

A disc-shaped retainer member 128 is configured to mechanically engage the retention flange 125 to secure the tag 120 to the ear. The retainer member 128 may include an array of radially extending ridges to facilitate user manipulation during attachment of the retainer member to the retention flange on the back side of the ear.

A cup-shaped backing member 130 is configured to be subsequently attached to the retainer member 128. The backing member 130 is configured as a quick-disconnect member so that, with a simple twist by the user, the backing member may be removed from and installed onto the retainer member. Suitable ridges may be provided for this purpose. For reference, the retainer member 128 and the backing member 130 are also sometimes referred to as a second attachment member or second attachment assembly.

As desired, optional thermal insulators 132 in the form of compliant discs may be sandwiched between the tag 120 and the retainer member 128. The insulators 132 may be soft, non-irritating material to help cushion the tag assembly elements and seal the respective ends of the aperture in the ear through which the shaft assembly 122 extends. Other elements may be installed as well, such as leaf springs or other retention members (not separately shown) to further ensure retention and comfort for the animal.

FIG. 3B shows a front facing view of the installed tag assembly 102. Only the tag 122 is visible from this vantage point, as shown in FIG. 2. The tag includes a circular shaped facing surface 134. A light emitting diode (LED) 136 or other user visual indication device can be placed in relation to the surface 134 to provide notification information regarding the status of the tag 122.

FIG. 3C is a back facing view of the installed tag assembly 120. This represents that portion of the tag assembly that can be viewed from behind the ear 114 in FIG. 2.

Figure 4:
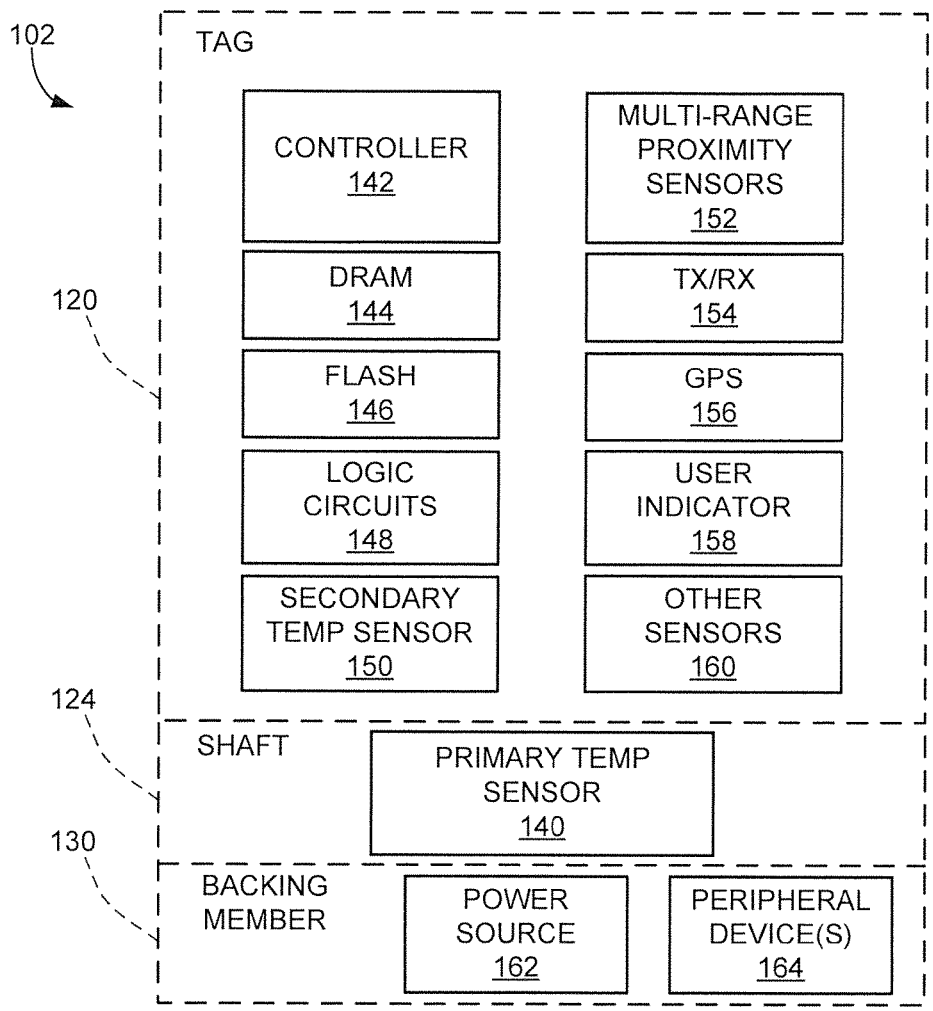
FIG. 4 is a functional block representation of the tag assembly of FIG. 3A in accordance with some embodiments.

FIG. 4 provides a functional block representation of various electrical components of the tag assembly 102 in accordance with some embodiments. Other arrangements can be used. The various elements may be realized using one or more integrated circuit (IC) devices mounted to a printed circuit board. Various interconnections are provided to enable intra-device communications, but such paths are omitted for clarity. Modes of operation of these various elements will be discussed more fully below.

Attention is initially directed to the shaft 124 which houses a primary temperature sensor 140. The primary temperature sensor, also referred to as a first temperature sensor, is configured to obtain temperature measurements correlated to an interior temperature of the outer ear of the animal by way of the surrounding ear material. The first temperature sensor 140 may take the form of a thermistor, a thermocouple, etc.

The tag portion 120 of the tag assembly 102 includes a controller 142, which provides top level control for the tag assembly 102. The controller 142 may be realized as one or more programmable processor circuits that utilize executable program instructions (e.g., firmware, software) stored in local memory. Additionally or alternatively, the controller may be a non-processor based hardware circuit such as an application specific integrated circuit (ASIC), field programmable gate array (FPGA), logic circuitry, etc. The controller 142 and related circuitry may be incorporated into a system on chip (SOC) device.

Local memory for the controller 142 includes volatile memory such as DRAM 144 and non-volatile memory such as flash memory 146. These respective memories may be used to accumulate measurement data, metadata and/or programming instructions, as well as any other data used by the device as required. A logic circuits block 148 represents other electrical elements including passive and active elements, gate logic, power regulators, switching devices, etc. used by the tag assembly.

A secondary temperature sensor 150 is used to obtain ambient temperature readings in an environment external to the animal. While the secondary temperature sensor is shown to be incorporated in the tag 102, the sensor may be housed elsewhere such as in the backing member 130. At least some embodiments operate to correlate changes between the respective temperature readings obtained from the first and second temperature sensors to monitor and assess a state of the animal. The various temperature measurements from the primary and secondary temperature sensors are stored locally in the tag 120, such as in the flash memory 146.

A number of multi-range proximity sensors 152 are used to provide different proximity indications based on different distances. A transmitter/receiver (TX/RX) circuit 154 communicates data to and receives data from other communication devices such as those shown in FIG. 1. An optional global position system (GPS) circuit 156 can be used to provide geoposition data relating to the tag.

A user indicator circuit 158 operates to provide user indications associated with the tag. This can include circuitry used to activate the LED 136 in FIG. 3B, as well as other indications as required (including audio/video/tactile indications, etc.). Block 160 represents additional sensors that may be incorporated into the tag to provide further environmental related measurements. As before, these and other data are stored locally on the tag as well.

The backing member 130 includes a power source 162, which may take the form of an electrical battery. While the use of a battery is contemplated, other power sources can be used including solar collectors, kinetic energy storage systems, etc. As desired, one or more peripheral devices 164 can be provisioned within the backing member 130.

Figure 5:
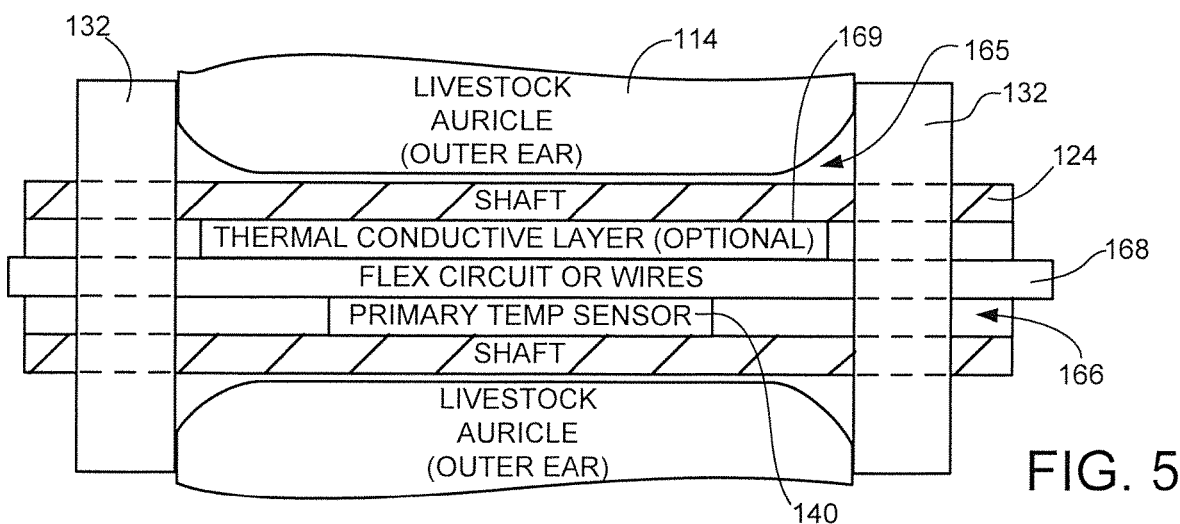
FIG. 5 is a schematic depiction of a shaft assembly of the tag showing various internal elements of interest in some embodiments.

FIG. 5 is a schematic cross-sectional representation of portions of the tag assembly 120 as installed within an aperture 165 that extends through the ear 114 auricle of the cow 112 (see FIG. 2). The cylindrical shaft 124 is hollow to provide a central interior passageway 166. Conductive paths 168 such as in the form of a flex circuit or insulated wires pass along the passageway 166 to provide power and data signals between the backing member 130 and the tag 120, as well as to provide the operable connections necessary for the primary temperature sensor 140.

An optional thermal layer 169 can be provided within the passageway 166. The layer 169 can be selected to have a thermal response that is different from that of ambient air. The layer 169 can be thermally insulative or conductive as required to facilitate accurate interior temperature measurements of the animal from the surrounding livestock ear (auricle). The thermal insulators 132 (FIG. 2) serve to thermally seal the opposing ends of the ear aperture 165 and stabilize the temperature readings obtained from the sensor 140.

It is noted that for livestock with large ears such as cattle, the outer ears (auricle) serve a number of functions including conductive cooling of the animal through contact of the ears with the surrounding atmosphere. Because the primary temperature sensor 140 is positioned to extend through the auricle, the primary temperature sensor 140 is configured to obtain accurate readings of an external ear or auricle temperature of the animal (also referred to herein as an outer ear temperature). This is in contrast to an internal body (or core) temperature of the animal. An internal body temperature measurement could be obtained, for example, by using an intrusive probe that extends into the animal's inner ear or otherwise is located at a suitable location within the main body of the animal such as through surgical implantation, ingestion, etc. It is known in the art that extending temperature probes into the inner ear can have a number of detrimental effects. Such probes can cause continued annoyance of the animal, can provide a possible source for contamination and infection, and can be easily damaged or dislocated.

While the auricle temperature will often be different from the body temperature, these two temperatures are often related and can be correlated. It is not necessary to obtain an actual internal body temperature measurement to achieve the various functions and features of the disclosed embodiments, since various temperature related states of the animal such as ovulation, sickness, heat stress, etc. can be readily detected using the non-intrusive sensors of the tag assembly 102 without the need or desire for a core temperature. Indeed, it has been found that some states of an animal can be determined specifically by monitoring auricle temperature fluctuations that may not be reflected in the main core body temperature.

Nevertheless, as desired an accurate estimate of the internal body temperature of the animal can be obtained from the auricle temperature readings using the primary temperature sensor 140 as well as the secondary ambient temperature sensor 150, other environmental sensors, etc. The tag assembly 102 can also be configured to communicate with other sensors (not shown) arranged to directly measure an internal body temperature of the animal.

Figure 6A:
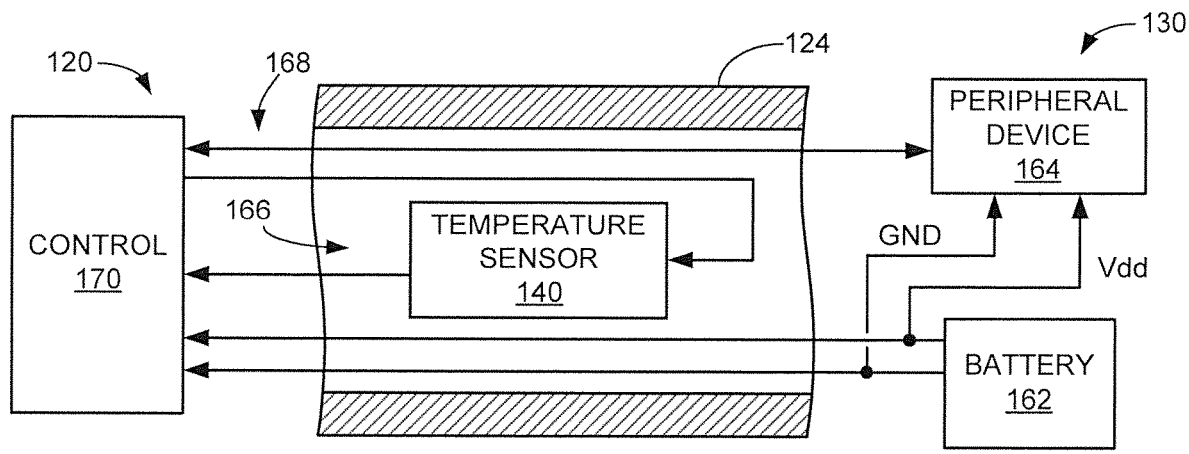
FIG. 6A shows an interconnection arrangement of various elements from FIG. 4, including the primary temperature sensor located within the shaft in some embodiments.

FIG. 6A is a functional block representation of electrical power and data signal pathways that extend between the tag 120 and the backing member 130. The power source (battery) 162 provides a positive rail voltage (Vdd) and a reference ground (GND) for use by circuitry in both the tag and the backing member via the conductors 168. A control circuit 170, which may include the controller 142 and/or other logic circuitry of the tag 120, supplies data control signals to the primary temperature sensor 140 within the shaft 124 and to the peripheral device(s) 164 in the backing member 130.

Figure 6B:
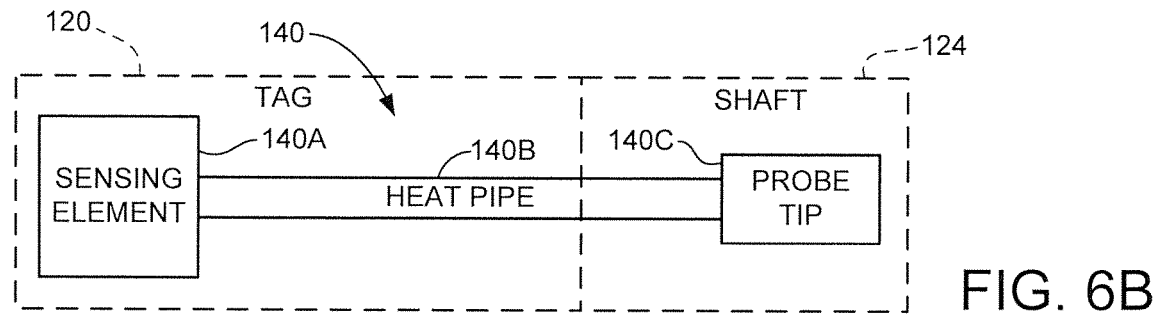
FIG. 6B shows another interconnection arrangement with the primary temperature sensor located within the shaft in accordance with other embodiments.

FIG. 6B shows an alternative arrangement to that of FIG. 6A. The primary temperature sensor 140 is still located within the shaft 124 as before, but takes a different configuration. The primary temperature sensor 140 includes a base sensing element 140A, and a thermally conductive heat pipe 140B that extends from the sensing element 140A and terminates at a probe tip 140C.

The sensing element 140A and the proximal end of the heat pipe 140B are disposed within the tag 120 (or alternatively, within the backing member 130). The distal end of the heat pipe 140B and the probe tip 140C are disposed within the shaft 124 as before. The probe tip 140C may be a separate thermally responsive element or may constitute the distal end of the heat pipe 140B.

Generally, the heat pipe 140B is a solid, hollow or fluid filled tubular member with a high rate of thermal conductivity that efficiently transports heat from the probe tip 140C to the sensing element 140A. In this way, the sensing element 140A outputs a thermal value indicative of the temperature observed at the probe tip 140C. In both of the cases of FIGS. 6A and 6B, it will be appreciated that the primary temperature sensor is disposed within the shaft 124 to sense the temperature at this location.

Figure 7:
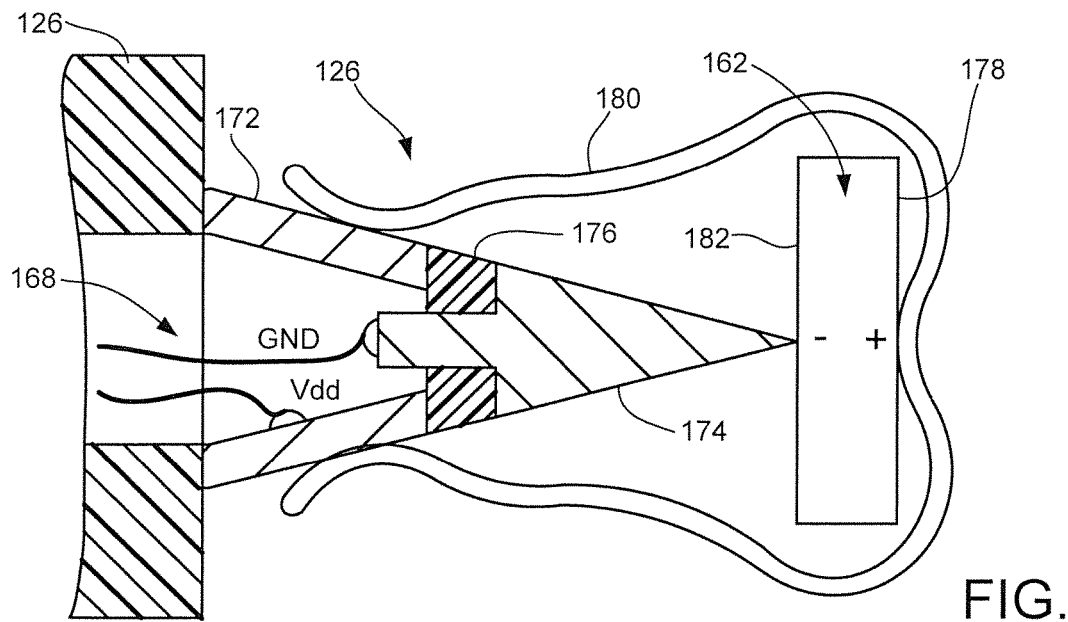
FIG. 7 illustrates a distal engagement arrangement of the system in some embodiments.

FIG. 7 is a simplified representation of an interconnection arrangement between the metal tip 126 at the distal end of the shaft assembly 122 and the battery 162. Other arrangements may be used so that FIG. 7 is merely illustrative. The tag assembly uses a headphone jack style interconnection so that the tip 126 is split into two electrically conductive segments 172, 174 which are electrically isolated via an intervening annular insulator 176. A positive terminal 178 of the battery 162 is electrically coupled to the first segment 172 using a conductive spring 180 or other interconnection mechanism. While a negative terminal 182 of the battery is shown to be directly coupled to the second segment 174, a second conductive spring or other interconnection mechanism can be placed in an intervening relation between these respective elements.

The battery 162 and spring 180 are configured to be housed within the retention member 130. With reference again to FIGS. 2 and 3A, it can be seen that an installation sequence for the tag assembly 102 can be carried out using a suitable installation tool (not separately shown) that grasps the tag 120, the retaining member 128 and the ear and punches the shaft assembly 122 through the ear so that the retaining member mechanically engages the flange 125 on the backside of the ear. The backing member 130 can thereafter be installed then or at a later time. The installation is carried out from the front facing surface of the ear 114, enabling the user to visually locate the tip 126 at a suitable target location for the central aperture 165 (FIG. 5).

Upon installation of the backing member 130, electrical power is supplied to the system and the tag assembly 102 becomes automatically activated. The controller circuit 142 initiates an initialization (boot) sequence and the tag transitions to an operationally ready mode during which data are collected from the various sensors and data communications are established and carried out as required. Energy saving schemes may be incorporated to extend battery life, such as placing the TX/RX circuits into a standby mode until a wakeup signal is received as the animal moves into proximity of a communication device. However, it is contemplated albeit not necessarily required that the various sensors will remain continuously on while the tag assembly is powered and the data from the sensors will be accumulated in the memory for subsequent download.

Figure 8:
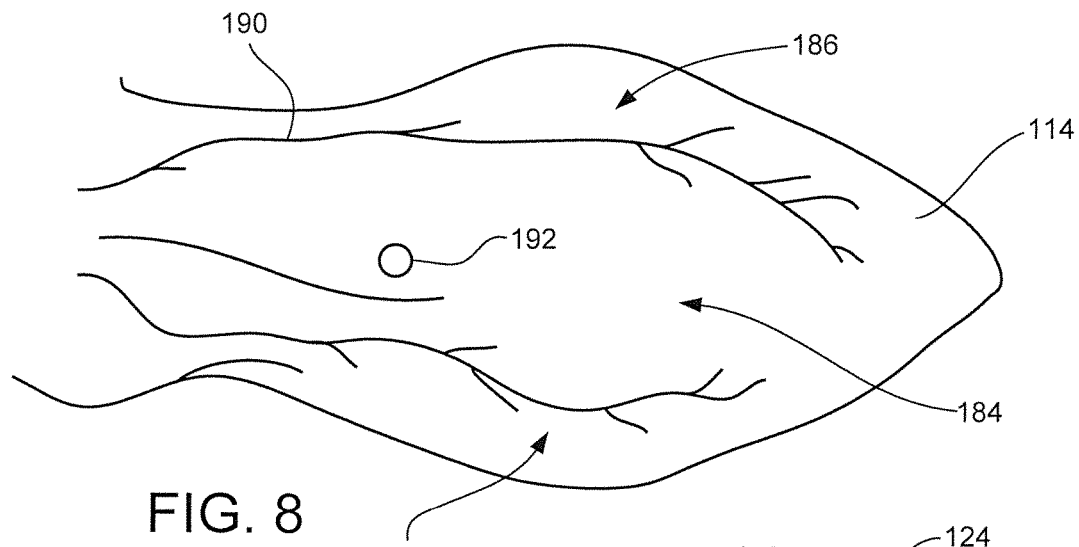
FIG. 8 is a schematic representation of the outer ear (auricle) of an animal to depict an appropriate location for the attachment of the tag assembly thereto in some embodiments.

FIG. 8 represents a typical bovine ear schematic for the outer ear (auricle) of a cow. A central cartilage region 184 is bounded by upper and lower vascular regions 186, 188 each having a network of blood vessels 190. Target location 192 represents a particularly suitable placement for the installation of the shaft portion of the tag assembly, although other locations may be selected. The target location 192 is just above the large blood supply provided by the lower vascular region 186.

Figure 9:
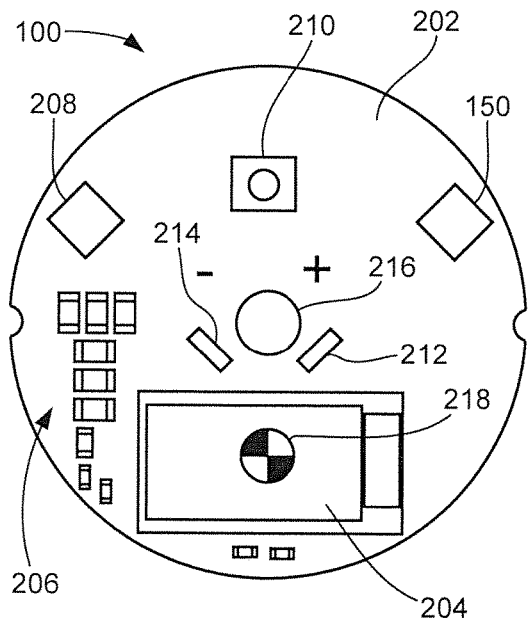
FIG. 9 shows a printed circuit board (PCB) supporting various components of the tag in some embodiments.

FIG. 9 is a representation of a printed circuit board assembly (PCBA) 200 disposed within the tag housing. A disc-shaped printed circuit board (PCB) 202 is provided with multiple layers of insulative material and signal traces (not separately shown) to interconnect various electrical components supported thereon. Representative elements include a system on chip (SOC) processing circuit 204, various discrete components 206, sensor integrated circuit (IC) 208, LED and driver circuit 210 and power terminals 212, 214. The secondary temperature sensor 150 is also shown. A central aperture 216 of the PCB 202 aligns with the axis of the shaft assembly 122 (FIG. 3A). The particular arrangement of the PCB 202 and the components thereon will depend on the requirements of a given application and thus can vary from the arrangement in FIG. 9. It will be noted from FIG. 9 that the center of gravity (COG) of the PCBA 200 will be below the central aperture 216, such as at COG marker 218, due primarily to the location of the SOC processing circuit 204 near the bottom of the PCB 202.

Figure 10:
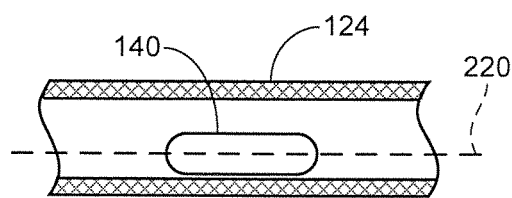
FIG. 10 shows an offset location of the primary temperature sensor within the shaft of the tag assembly in some embodiments.
Figure 11:
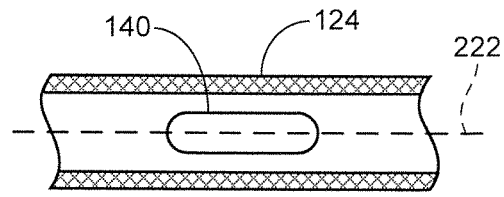
FIG. 11 shows a centered location of the primary temperature sensor within the shaft of the tag assembly in further embodiments.

FIGS. 10 and 11 show respective side elevational schematic representations of the medial portion of the shaft 124 and primary temperature sensor 140. In FIG. 10, the temperature sensor 140 is biased toward the lower portion of the shaft along offset axis 220, while in FIG. 11 the temperature sensor 140 is nominally centered along axis 222 which nominally aligns with the central axis of the shaft. These or other relative placements of the temperature sensor within the shaft may be used as desired. Placement of the sensor 140 toward the bottom of the interior of the shaft places the sensor closer to the lower vascular region 188, potentially providing more accurate readings of the interior ear temperature of the cow.

Figure 12:
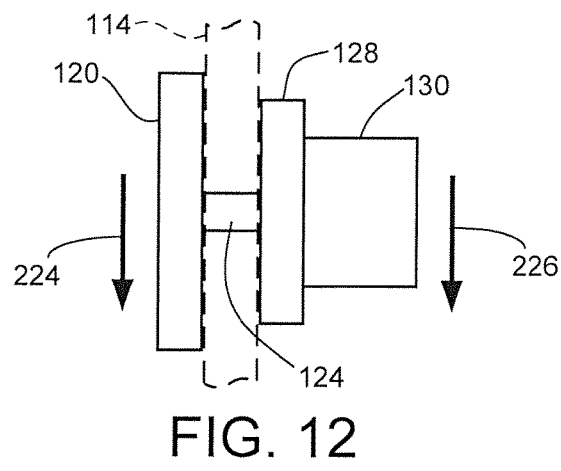
FIG. 12 illustrates bias forces applied to the tag assembly after installation.

FIG. 12 is a simplified representation of the installed tag assembly 102 in the ear 114 of FIG. 8. Arrows 224 and 226 show the downwardly directed bias forces that will generally be imparted by the tag assembly due to the effects of gravity. The tag assembly 102 is generally "balanced" in that the mass of the backing member 130 (which includes the battery 162 and, for purposes of this discussion, the retention member 128) will be somewhat matched by the mass of the tag 120.

The ratio of mass between the tag 120 and the backing member 130 can vary as required; a substantially 50%-50% tag/backing member ratio would be optimal, but other ranges can be used such up to about 70%-30% tag/backing member, or down to about 30%/70% tag/backing member.

This balanced approach provides at least two benefits. First, improved comfort is provided to the animal since the tag is not being pulled forward or backward to a significant extent due to a large imbalance between the front and the rear of the tag assembly. Second, this arrangement provides a measure of self-centering of the location of the primary temperature sensor relative to the vascular region 188, ensuring more accurate and consistent ear temperature readings.

To this latter point, the mass of the tag, along with the lower location of the COG 218 for the PCBA 200, tends to maintain the shaft 124 biased toward the bottom of the ear hole aperture 165, providing enhanced thermal contact between the primary sensor 140 and the vascular aspects of the ear 114. To the extent that movement, nuzzling, etc. causes rotation of the tag assembly 120, such will be corrected as gravity realigns the assembly as represented in FIG. 9 so that the SOC 204 is nominally oriented at the bottom of the tag 120. In this way, the primary temperature sensor 140 (see FIGS. 10-11) will be maintained in a desired relation to the ear, leading to more consistent temperature measurements over time.

The tag assembly 102 is characterized as a permanent or lifetime tag since the battery or other power source can be replaced on a regular basis, such as annually. This can be carried out as discussed above through the simple expedient of removing (e.g., twisting off) the backing member 130, replacing the battery, and replacing the backing member (e.g., twisting on). The retainer member 128 maintains the tag 120 and shaft 124 in place during this operation. The various dimensions can be sized to accommodate growth of the animal over its life cycle. The tag can also be temporarily disabled by removing the retainer member 130 during times in which data collection and/or energy consumption is undesirable such as during animal transport, etc. In other embodiments, a user selectable feature can be incorporated into the communication devices (see FIG. 1) to remotely activate and deactivate the tag as desired.

Figure 13:
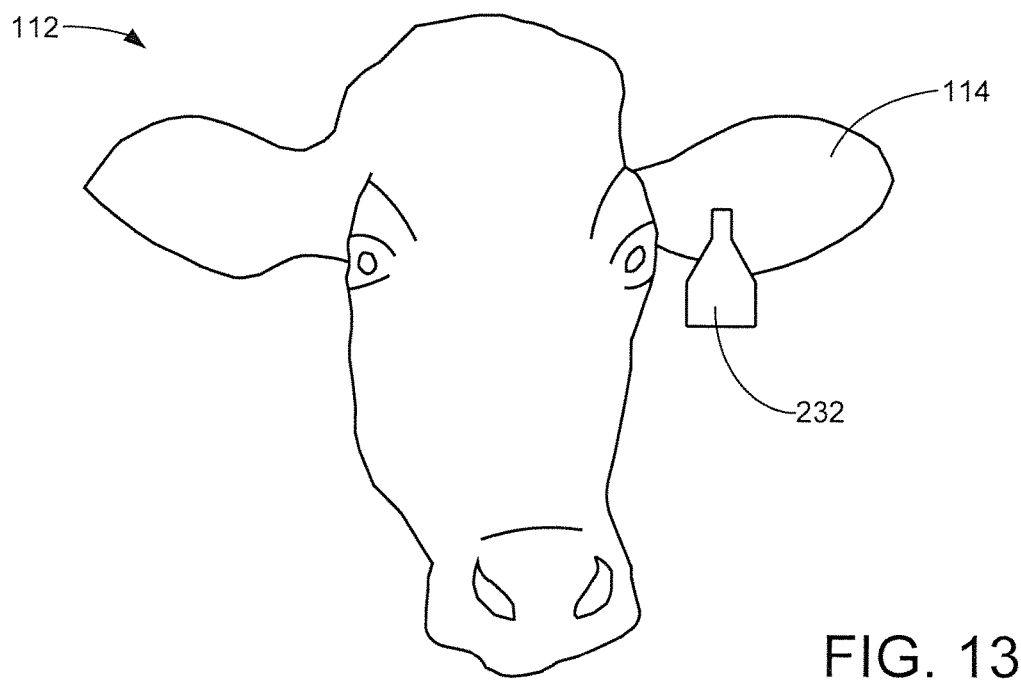
FIG. 13 shows another schematic depiction of another cow having a tag assembly from the system of FIG. 1 in accordance with further embodiments.

FIG. 13 shows the cow 112 of FIG. 2 with another tag assembly 232 in accordance with further embodiments. The tag assembly 232 is functionally similar to the tag assembly 102 and has the various constituent elements discussed above such as in FIGS. 4 and 5. The tag assembly 232 is characterized as a temporary or one-use tag for a shorter time duration, such as animals that are raised and fattened in a feed lot or similar environment. Other configurations can be used so FIG. 13 is merely illustrative and not limiting.

Figures 14A, 14B:
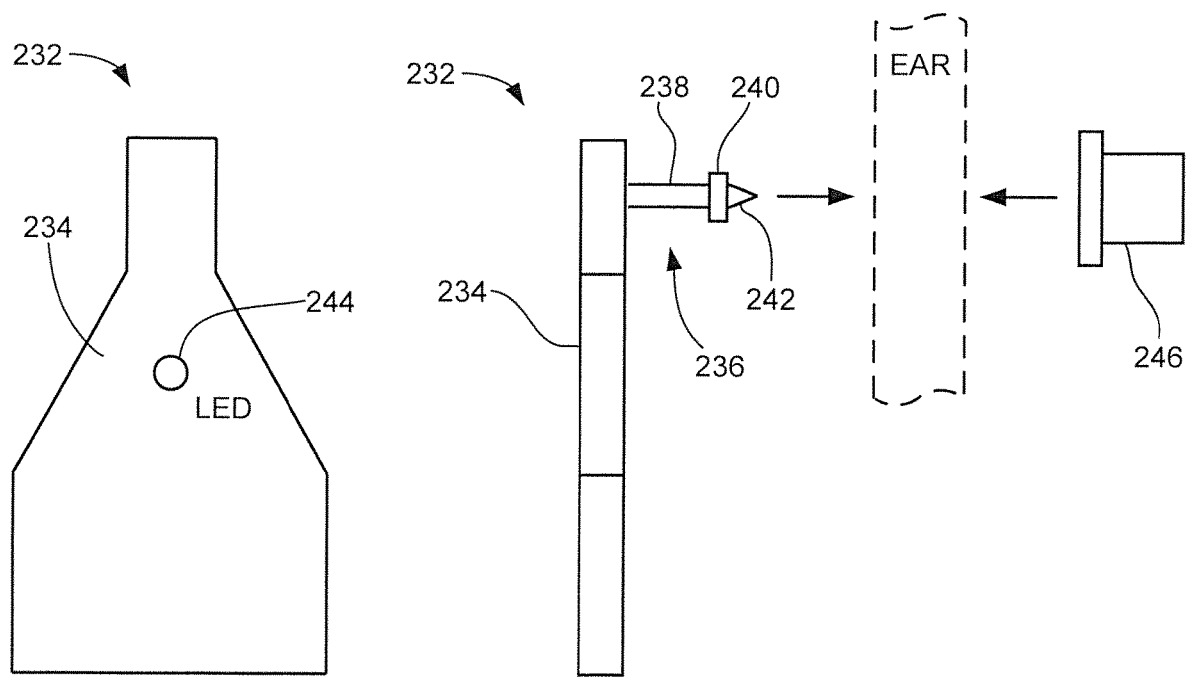
FIGS. 14A and 14B show respective front facing and side elevational views of the tag assembly of FIG. 13.

FIGS. 14A and 14B show front facing and side elevational views of the tag assembly 232. As before, the tag assembly 232 includes a tag (main body or primary attachment member) 234, shaft assembly 236 with shaft 238, retention flange 240, metal tip 242 and LED indication device 244. A backing member 246 is configured to engage the flange 240 to permanently secure the tag assembly 232 to the animal. Alternatively, the backing member 246 can be configured to be removably replaceable as required.

As before, the primary temperature sensor 140 is disposed within a central passageway in the shaft 238 to obtain ear temperature measurements from the animal. The power source 162 (battery) may be disposed within the body of the tag 234 rather than in the backing member 246, although such is not required. For clarity, the continued discussion below of additional features of the tag assembly will be described in terms of the permanent tag assembly 102, but it will be understood that these same features can be readily incorporated into the temporary tag assembly 232 as well.

Figure 15:
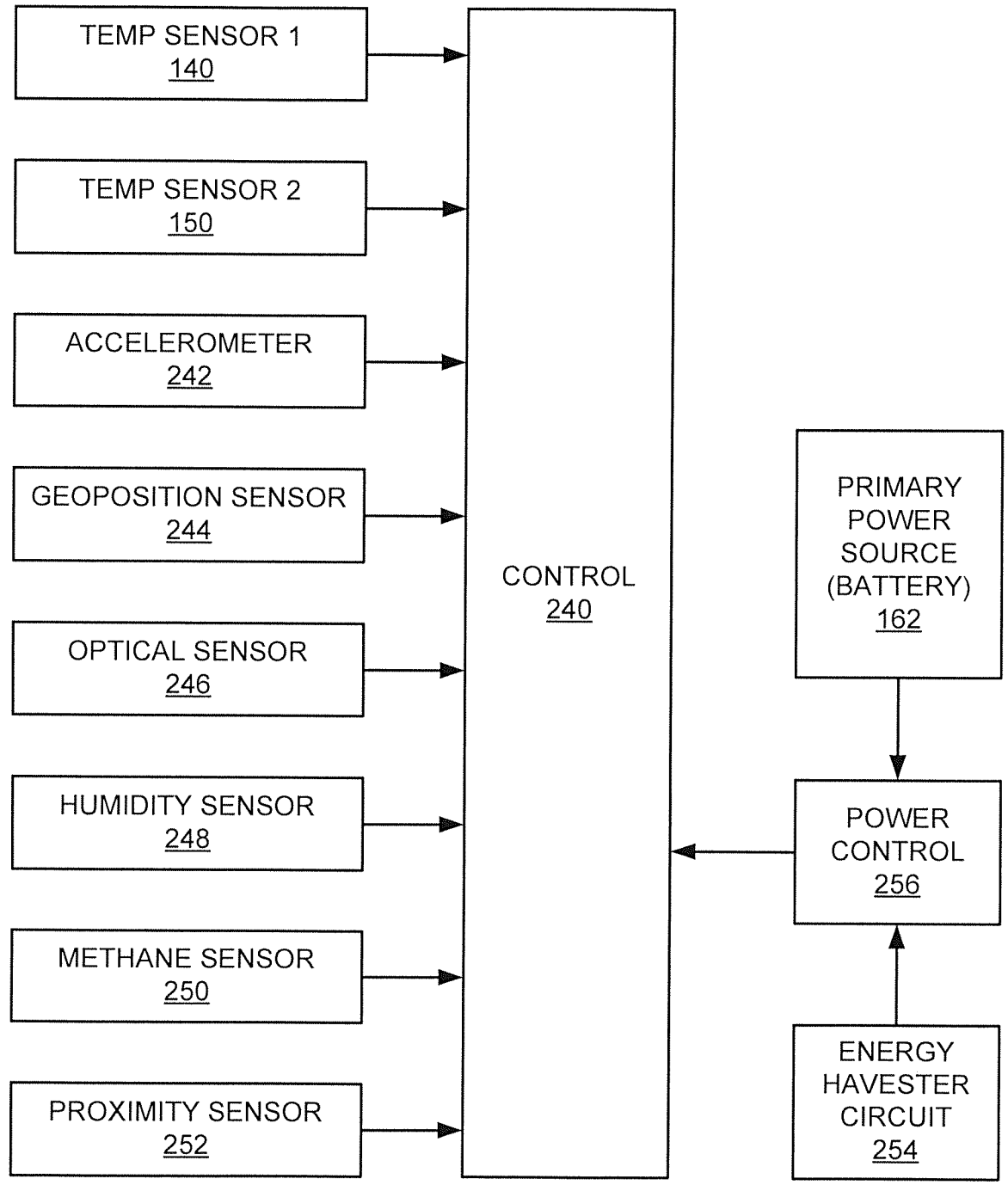
FIG. 15 illustrates various sensor inputs and energy source inputs that may be incorporated in the respective tag assemblies of FIGS. 2 and 8.

FIG. 15 shows a functional block representation of various sensor inputs that can be utilized by the tag assembly 102. A central control circuit 240 may be realized by the aforementioned programmable processor or other circuitry of the tag. Sensors include the first (primary) temperature sensor 140, the second (secondary) temperature sensor 150, a multi-axis (e.g., x, y, z) accelerometer 242, a geoposition sensor 244, an optical sensor 246, a humidity sensor 248, a methane sensor 250, and a proximity sensor 252. Other sensor configurations can be used including fewer sensors than those shown in FIG. 15, as well as additional sensors as desired. The various sensors provide indications of the status of the animal and the surrounding environment. The sensors may be disposed within the tag 120 or the backing member 130 as desired.

Power is supplied to the control circuit 240 and other aspects of the tag assembly by the power source (battery) 162. Other power generation mechanisms can be included in the tag assembly such as represented by an energy harvester circuit 254, which can take the form such as a solar collector, kinetic energy converter, etc. A power control circuit 256 can be used to regulate and condition the power from the respective devices 162, 254.

Figure 16:
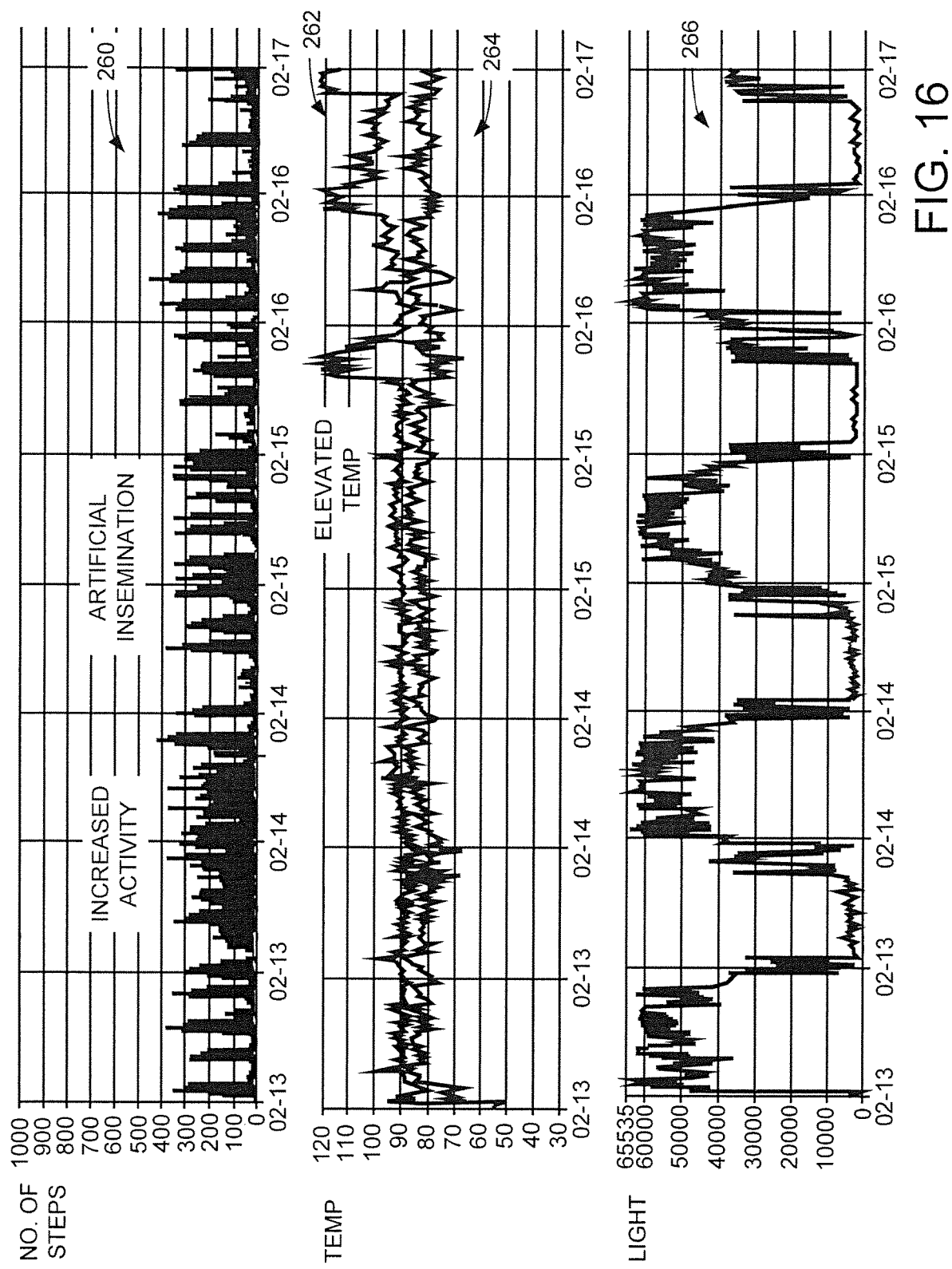
FIG. 16 is a graphical representation of data obtained from a selected tag assembly in accordance with some embodiments.

FIG. 16 shows combined graphical data outputs of real world data from an installed tag assembly for a selected cow over a particular time interval. The data were collected by the tag assembly and transmitted to another device as in FIG. 1 for analysis and display.

The graphical data outputs include an activity waveform 260, a primary temperature waveform 262, a secondary temperature waveform 264 and a light waveform 266. Each of the waveforms is plotted against a common x-axis indicative of elapsed time over a period of several days. Other sensor outputs (see FIG. 15) can be readily combined with these waveforms for display as required.

The activity waveform 260 represents the output from a selected sensor such as the accelerometer 242 to indicate activity by the cow (in this case, number of steps taken by the animal). The primary temperature waveform 262 shows temperature measured by the primary temperature sensor 140. The secondary temperature waveform 264 shows temperature measured by the secondary temperature sensor 150. The light waveform 266 shows day/night cycling over the associated time interval obtained from the optical sensor 246.

Each high region in the light waveform 266 generally corresponds to a daylight period and each low region in the light waveform generally corresponds to a nighttime period. The corresponding interval is thus a little over four (4) consecutive days, or about 100 hours, from February 13 to February 17.

As can be determined from an examination of FIG. 16, the animal experienced a higher than baseline amount of activity beginning in the night of the first day (February 13) and through the daylight hours of the second day (February 14). A baseline difference (delta) between the first and second temperature readings (waveforms 262, 264) remained constant during this interval, although a slight decrease in internal temperature (waveform 262) is indicated.

This enhanced physical activity was interpreted as an indication that the cow was ovulating. An artificial insemination operation was subsequently applied to the cow in response to this indication, which was followed by elevated temperature readings showing large divergences between waveforms 262 and 264. The temperature exclusions of the outer ear temperature of the cow signify hormonal changes that were experienced by the cow, indicating that the insemination operation was successful.

By monitoring the differences between the respective first and second temperature sensors 140, 150, a health status of the animal (in this case, pregnancy) can be readily determined. Other health related statuses can be determined as well, such as sickness, heat stress, etc. based the relative magnitudes of these two readings and the differences therebetween, particularly when correlated to other waveforms from other sensors. Using two sensors in this manner helps to more accurately assess the actual state of the animal, since differences in ambient temperature conditions can contribute to changes in the ear temperature of the animal. By tracking both temperatures, the magnitudes of the respective temperatures as well as the differences between the respective temperatures can provide valuable information for livestock management efforts.

Figure 17:
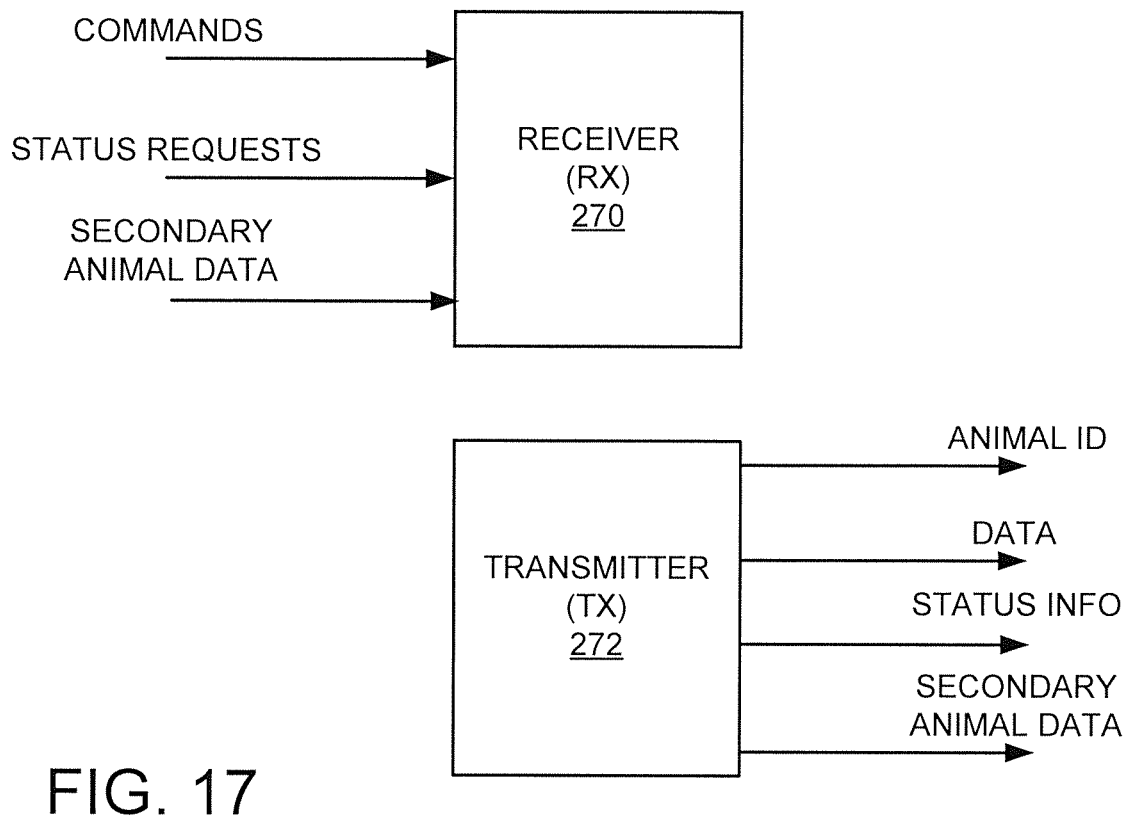
FIG. 17 is a functional block representation of transmitter (TX) and receiver (RX) capabilities of the tag assembly in some embodiments.

FIG. 17 shows a receiver (RX) circuit 270 and a transmitter (TX) circuit 272 of the tag assembly 102 in accordance with further embodiments. The respective circuits 270 can be configured to communicate via one or more wireless communication protocols including Bluetooth, Wi-Fi, Cellular networks, wireless Ethernet, etc. The receiver circuit 270 can be configured to receive a number of different types of data including commands, status requests and data collected from a different nearby tag for a secondary animal, including the types of data discussed above in FIG. 16.

The transmitter circuit 272 can be configured to transmit various types of data including an animal (tag) identification (ID) value, data collected by the tag, status information regarding various events, data transfers, etc., and secondary animal data received from a nearby tag associated with a secondary animal. Other forms of data communications can be carried out by each tag so the examples in FIG. 17 are merely exemplary.

Figure 18:
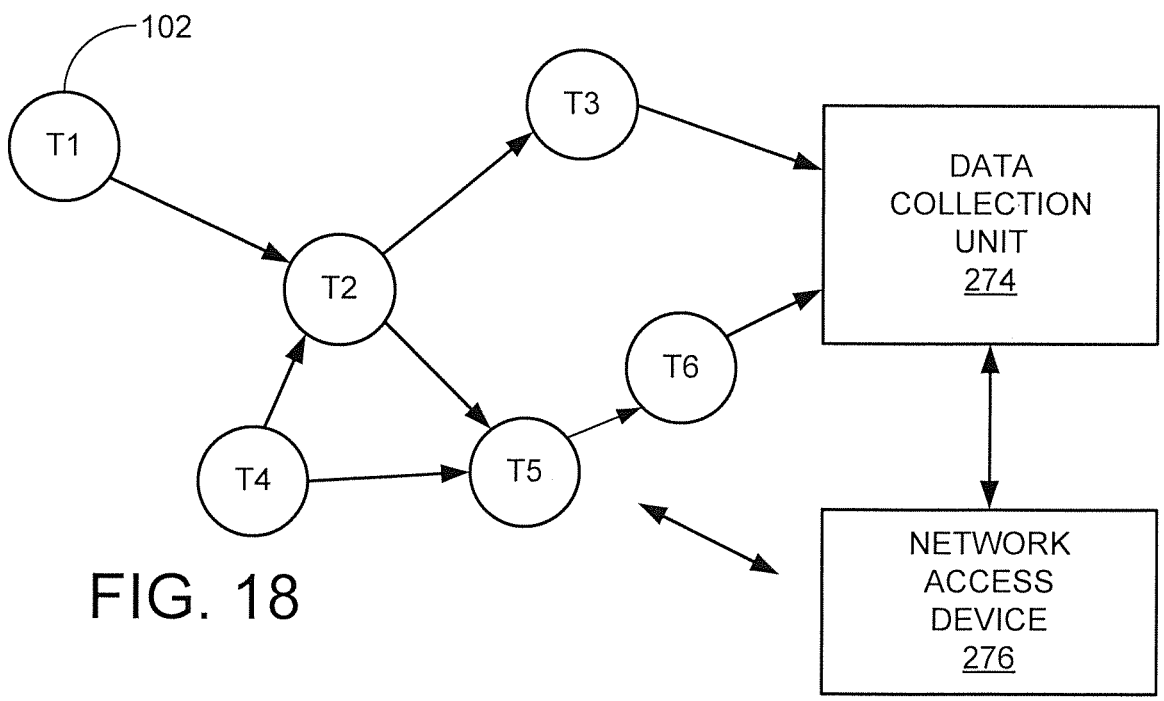
FIG. 18 is another functional block representation to depict mobile herd network capabilities of the tag assemblies.

FIG. 18 shows a mobile herd feature of the tag assemblies in some embodiments. Six (6) tags identified as tags T1 through T6 are affixed to corresponding animals who are located in relative positions with respect to a data collection unit 274. The data collection unit 274 may correspond to the unit 104 in FIG. 1 and may be a passive receiver or a two-way communication device able to both collect data from the various tags as well as to transmit the collected data to another device.

The unit 274 may be placed at an appropriate location where the animals routinely gather, such as watering or feed troughs, corrals, barns or other shelters, milking machines, gates, etc. In some cases, the tags T1-T6 are configured to sense when the animal is within receiving range of the unit 274 and commence uploading of collected data from the various sensors that have been stored in the local tag memory (e.g., flash, DRAM, etc.).

As shown by FIG. 18, in some cases the closest tag or tags to the unit 274 establish an inter-tag communication and data transfer event whereby the closest tags (in this case, tags T3 and T6) download data associated with their own animals, followed by transmitting commands to other near-neighbor tags in the area to request and forward data from these other tags. In some cases, data may be received by the unit 274 multiple times through different pathways (e.g., data from tag T1 may be reported by both T3 and T6, etc.) but this is not an issue as the data collection unit indexes the received data and can discard duplicate data sets. The data pathways can also be used to provide information with regard to herd dynamics and arrangements.

The unit 274 may assign timestamps or other identification information with each data transfer session. The tags may similarly mark data as having been transferred and may retain the data for a set period of time or until the tags receive a clear command to clear data sets that have been successfully uploaded to the system.

A network access device 276, which may correspond to the devices 106 in FIG. 1, can be used to subsequently upload the data from the unit 276. The device 276 is contemplated as comprising a portable network accessible device with wireless communication capabilities, such as a smart phone, tablet, laptop, etc. A wired data connection pathway (e.g., plug-in cable) can alternatively be used so the references to wired networks is illustrative but not limiting.

The data obtained from the device 276 can in turn be transferred to another device such as a local computer, remote server, etc. or utilized locally without further data transfer as desired. Other arrangements can be used including using the network access device 276 to poll the data from the herd network directly without the use of the intervening data collection unit 274. In still other arrangements, the unit 276 can directly communicate the data to a remote computer, server, etc.

Figure 19:
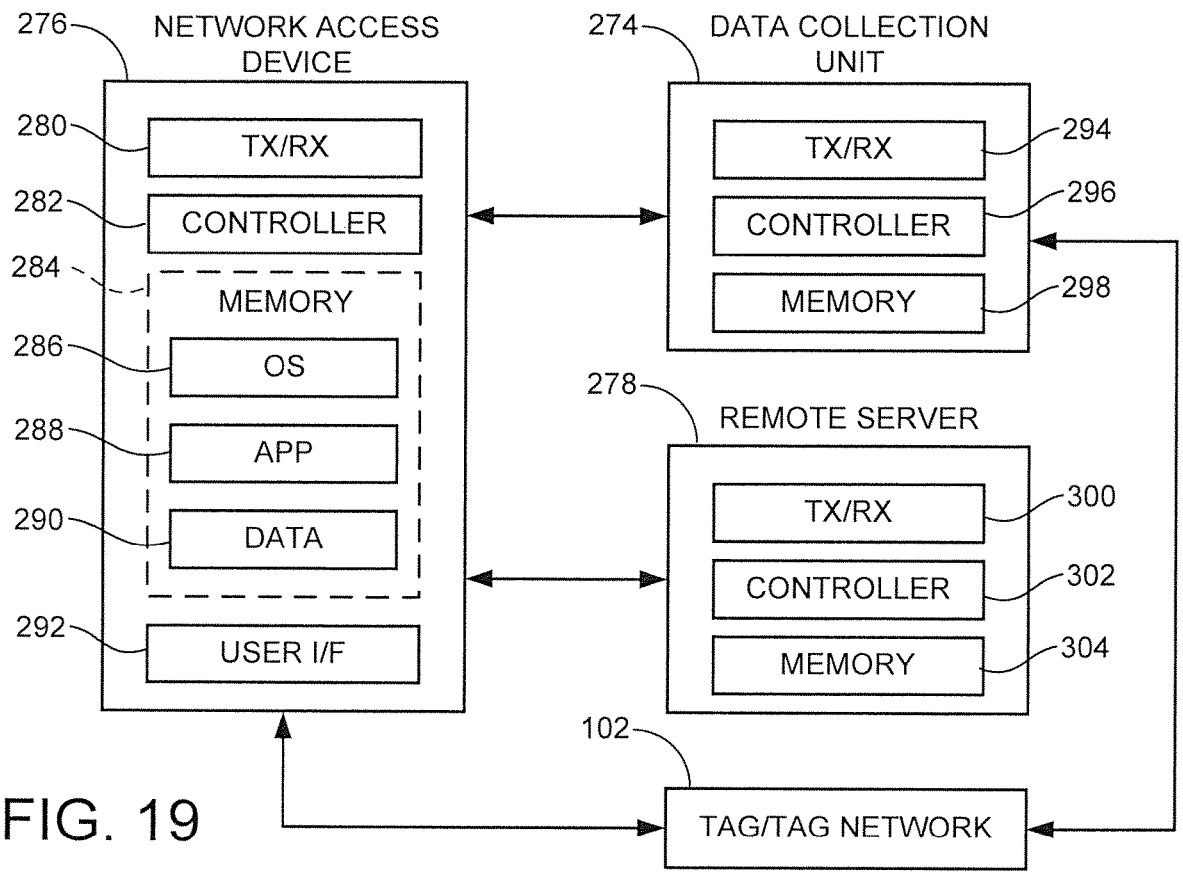
FIG. 19 is a functional block representation of the system in accordance with further embodiments.

FIG. 19 shows the network access device 276 in conjunction with the data collection unit 274, a remote server 278 and a population of tags on associated animal. Network communications can occur for individual tags or a group of tags forming a tag network as in FIG. 18.

In FIG. 19, the device 276 is contemplated as comprising a smart phone type device having TX/RX circuitry 280, a controller circuit 282 and memory 284. The memory stores various programming instructions and data structures including an operating system (OS) 286, an application program (app) 288 configured to enable communications with the other devices in FIG. 19, and data 290 collected from the tag(s) and other devices as required. A user interface (I/F) 292 includes a suitable graphical user interface such as a touch screen display, keyboard, etc. to enable the user to interact with the other devices. Other features may be included as well including power supply, audio/video recording features, etc. that may be user selectable as desired.

The data collection unit 274 is a stand-alone passive data receiver unit with a TX/RX circuit 294 that broadcasts signals in a relatively small area (e.g., 30 feet or so via the Bluetooth specification) to detect both the tags 102 and the device 276 and automatically synchronize with these components. A controller circuit 296 and associated memory 298 may be used to direct data, command and status upload/download operations. It is contemplated that the data collection unit may be associated with or incorporated into other equipment, such as a milking machine in a dairy farm, etc.

The server 278 may likewise include TX/RX circuitry 300, a controller circuit 302 as one or more programmable processors and memory 304. In some cases, history data is archived by the memory 304 to provide long term storage and analysis capabilities of the data. Data analyses and reporting can be performed on the data at both the device 276 and server 278 levels as required.

Figure 20:
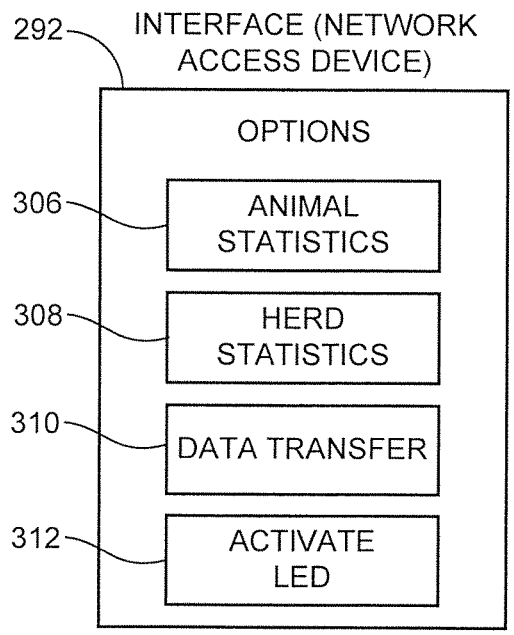
FIG. 20 shows an exemplary user interface that may be displayed on the network access device of FIG. 19.

FIG. 20 shows a user interface screen of the user I/F 292 that can be displayed by the execution of the app 288 in some embodiments. Various options can be provided, each accessible via the touch screen display or via some other mechanism. Animal statistics are represented at 306. User selection of this feature will result in the display of various statistics collected for a selected animal/tag, such as but not limited to the various sensor data discussed above in FIGS. 15-16. The data can be displayed in various ways including tabular, graphical, etc.

Herd statistics are represented at 308. Selection of this feature result in the display of accumulated statistics for the herd (e.g., data collected from all or a selected portion of the tags in the system), such as averages, outliers, etc. In some cases, map data indexed against elapsed time or other features can be used to provide an indication of the location of the herd over a period of time. For example, correlating geoposition data can provide a graphical representation of the locations of the herd throughout a particular data in a simulated map format, etc.

A data transfer feature 310 enables data to be uploaded to other devices and/or the downloading of available data from various tag assemblies 102. The data sets collected by the various devices are appended with header information to signify which data have been collected at various times/locations, allowing provenance data to be accumulated for verification purposes as well as to enable the tags to only transmit newly collected data that have not already been archived by the system.

An activate LED feature 312 enables the user to selective activate the LED user indication device (e.g., 136, FIG. 3B; 244, FIG. 14A) at appropriate times. For example, if a particular animal is desired to be located quickly from within a closely arranged herd, illuminating (either solid or blinking) the LED can allow the handlers to visually identify the target animal.

Similarly, other status information can be provided as well; during a vaccination operation in which each member of the herd is processed in turn, the light can be activated for each animal who has been treated (or needs to be treated), ensuring the handlers apply the required processing to every animal in turn without missing any. Multi-colored LEDs that can be activated to show different colors (e.g., red, green, blue, etc.) can be used for a variety of purposes to signal different status conditions. While the present discussion contemplates user activation of the LED (or other indicator), in other embodiments the individual tag assemblies 102 can be configured to activate the LEDs under various circumstances.

Figure 21:
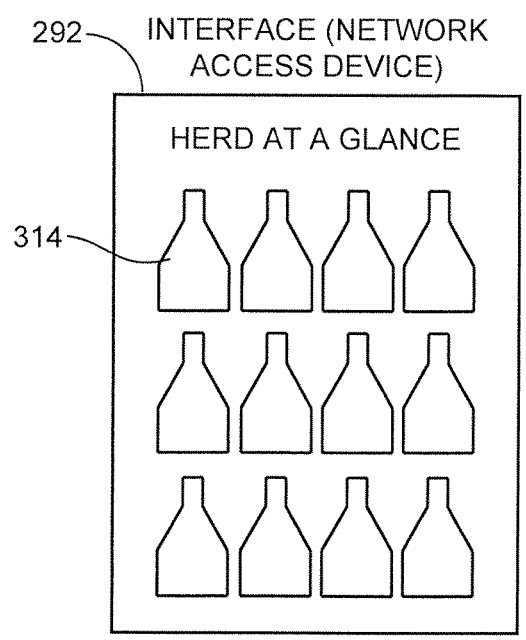
FIG. 21 shows another exemplary user interface that may be displayed on the network access device of FIG. 19.

FIG. 21 shows another display arrangement for the user interface 292 on the network accessible device 276. This screen shows a herd at a glance feature where each of the tags/animals for a given herd can be listed in turn, allowing a user to scroll through and select an individual tag/animal for further processing. Status data for the various animals can be indicated on this screen as well. Other features, analyses and information can be displayed as desired so FIGS. 20 and 21 are merely exemplary of the types of real-time and history data that can be obtained from the tag assemblies 102.

Figure 22:
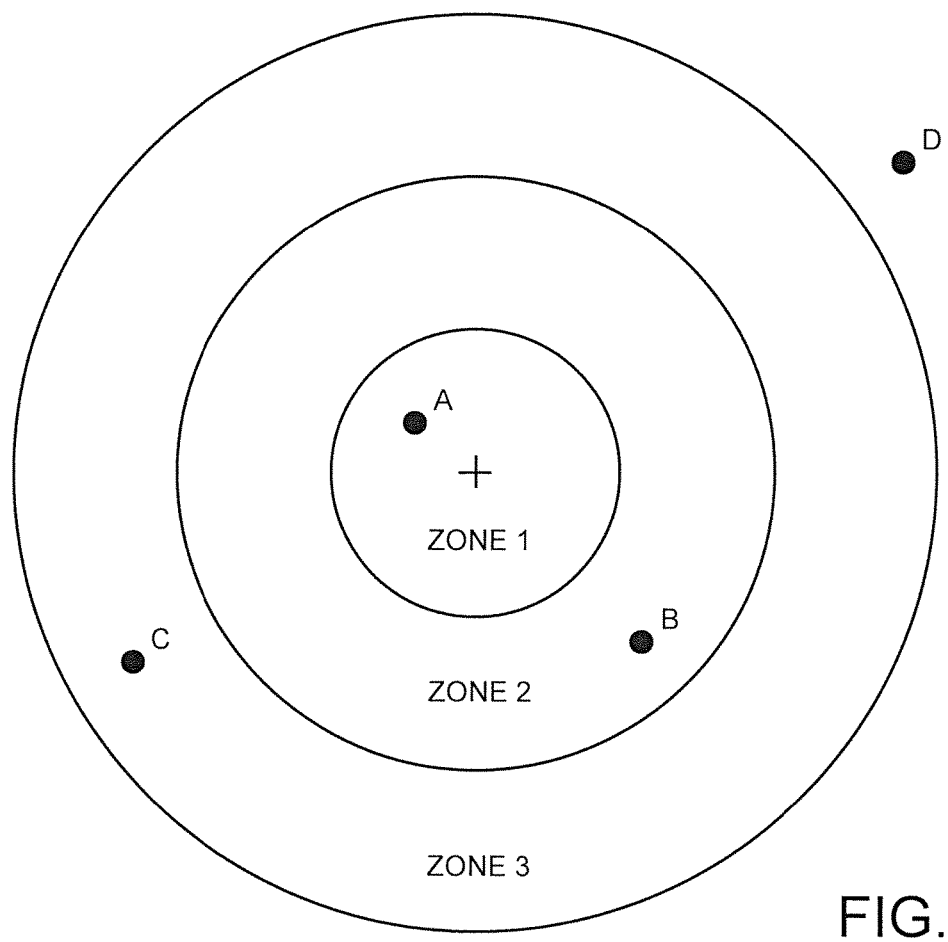
FIG. 22 shows various communication zones that may be established for the system.

FIG. 22 shows additional aspects of the tag assemblies 102 in some embodiments. Different geographical zones can be defined based on various system parameters. Three such zones are denoted as Zones 1 through 3. The zones are concentric but such is merely exemplary. Zone 1 may represent a short range location, such as within the communication range of a selected data collection unit 274 (e.g., near a feeding trough, watering hole, etc.). Zone 2 may be a farther distance from Zone 1 and may be defined by an array of other data collection units of various types in and around a selected area in which the animals are permitted to roam. Zone 3 is yet another zone and may define the outermost bounds of the acceptable area for the animals to roam, such as the boundaries of a field, pasture or other open area. Other, higher power elements may be used to denote the boundaries of the third zone, including but not limited to Wi-Fi routers, etc. Location of the animals within the zones can be carried out in a variety of ways including proximity sensors, GPS detection, triangulation using multiple data collection units, etc. Mobile data collection and sensing units can be used, including drones, vehicles, personnel carrying hand-held or vehicle mounted data collection units, data collection units attached to herd dogs or other service animals, etc.

Point A indicates a selected animal/tag combination located within Zone 1, Point B within Zone 2, Point 3 within Zone 3 and Point D being beyond Zone 3. Different protocols may operate with respect to the location of the animal/tag at these respective points, including proximity of tags to other tags which in turn have been located using other mechanisms.

Figure 23:
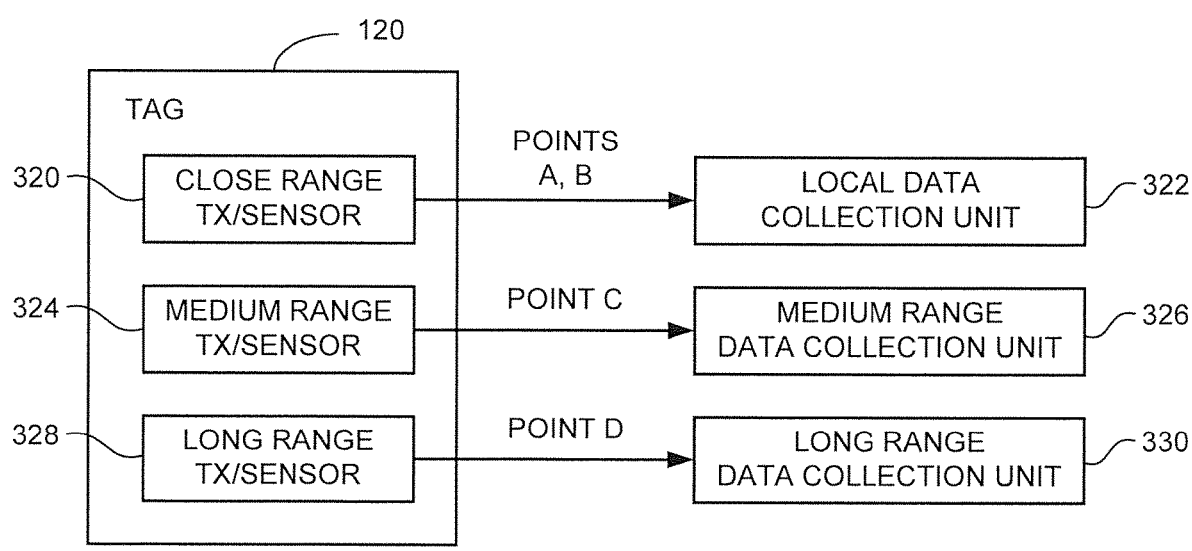
FIG. 23 illustrates communications carried out by different communication circuits of the tag in relation to the various zones of FIG. 22.

FIG. 23 shows operation of a selected tag 120 at each of these respective points. In some cases, a close range TX/sensor 320 operates at relatively short ranges such as Points A and B to communicate with a local data collection unit 322. A medium range TX/sensor 324 communicates with a medium range data collection unit 326, and a long range TX/sensor 328 communicates with a long range data collection unit 330. In some cases, the respective sensors/collection units can be configured to detect when the animal crosses various boundaries between zones, and provide the requisite notification to a home base. The long range TX/sensor may be a cellular telephone type device that calls home if the animal crosses the boundary to Zone 3. This circuit may normally be inactive, but becomes activated based on detection of the crossing of the boundary to Zone 3.

Figure 24:
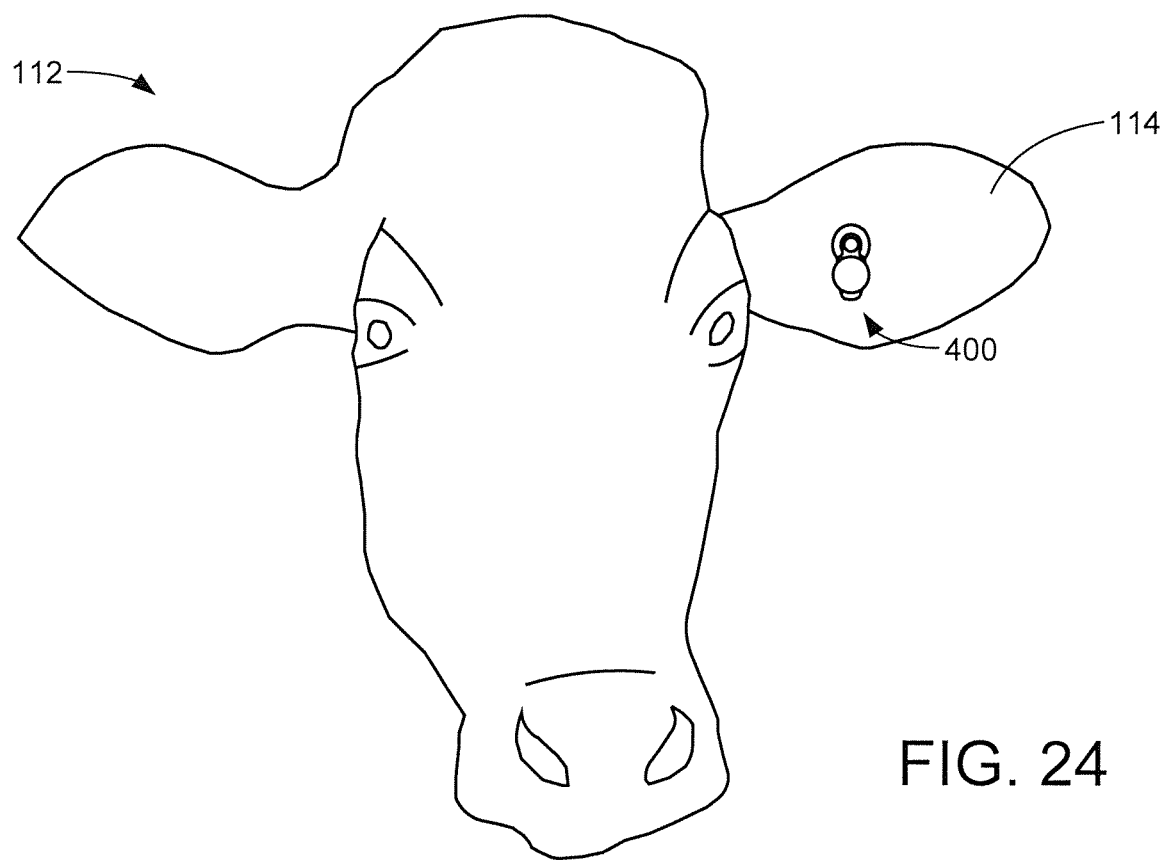
FIG. 24 shows a schematic depiction of another animal (cow) having a tag assembly constructed and operated in accordance with further embodiments.

FIG. 24 shows the cow 112 of FIGS. 2 and 13 with yet another tag assembly 400 in accordance with further embodiments. The tag assembly 400 is characterized as a lifetime tag assembly that can be utilized for an extended period of time, including being moved from one animal to the next as required. Other configurations can be used so FIG. 24 and following are merely illustrative and not limiting. The tag assembly 400 is configured to be installed in the same general location as discussed above in FIG. 8.

Figure 25:
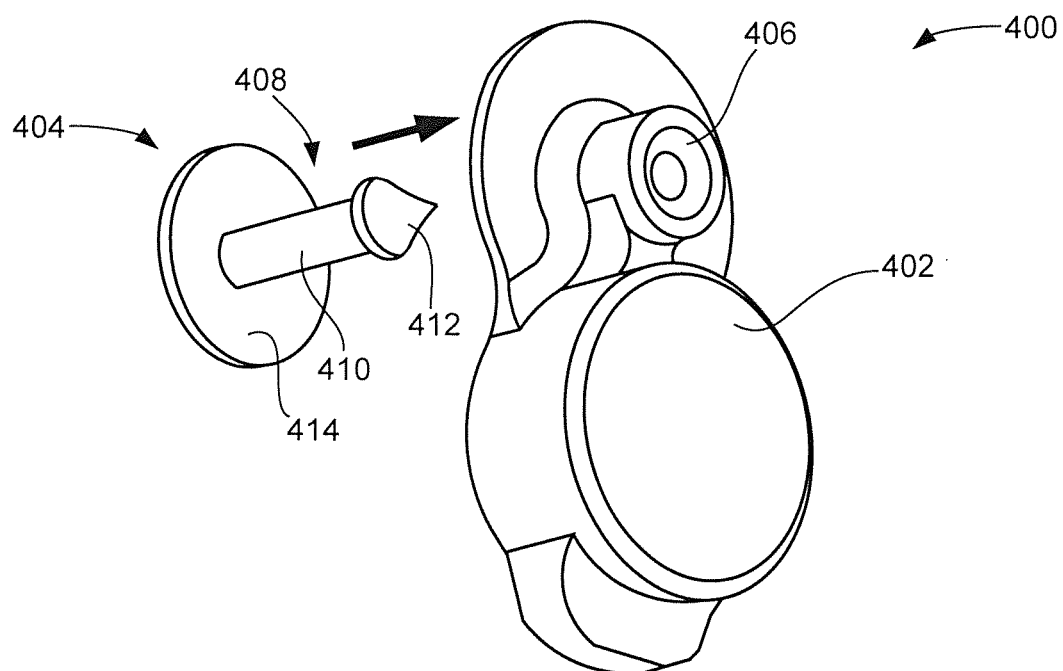
FIG. 25 is an isometric representation of the tag assembly from FIG. 24 in conjunction with a connection member.

FIG. 25 shows the tag assembly 400 to include a forward facing tag 402 and a rear facing connection member 404. The tag 402, also referred to as a tag member, a base member and a first attachment member, has a through hole aperture 406. The connection member 404 is also referred to as a connector, a backing member and a second attachment member, and has a shaft assembly 408 that insertingly aligns with the aperture 406. The shaft assembly 408 includes an elongated cylindrically shaped shaft 410 and a piercing tip member 412. The piercing tip member 412 has a diameter greater than that of the shaft 410 and is configured to pierce the auricle (outer ear) 114 of the cow 112 and be secured within the interior of the aperture 406. The length of the shaft 410 generally establishes the final relative distance between the tag 402 on one side of the ear and a disc-shaped base 414 of the connection member 404 on the other side of the ear.

Figure 26A:
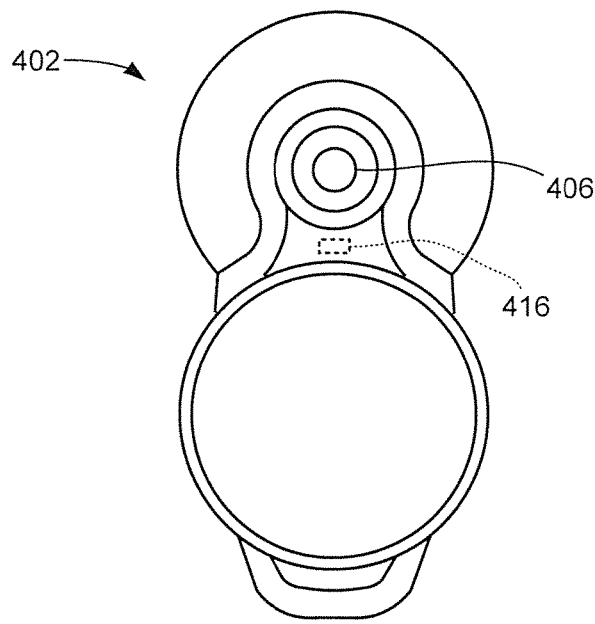
FIGS. 26A and 26B provide respective front and rear facing views of the tag assembly of FIG. 25.
Figure 26B:
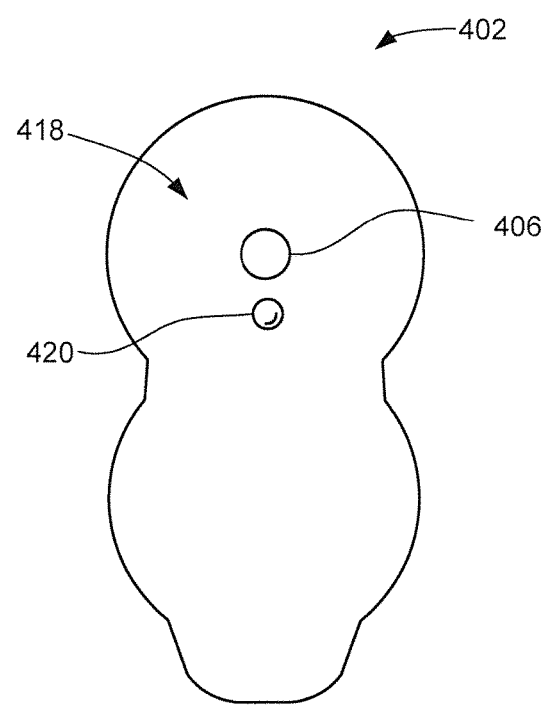
Figure 26C:
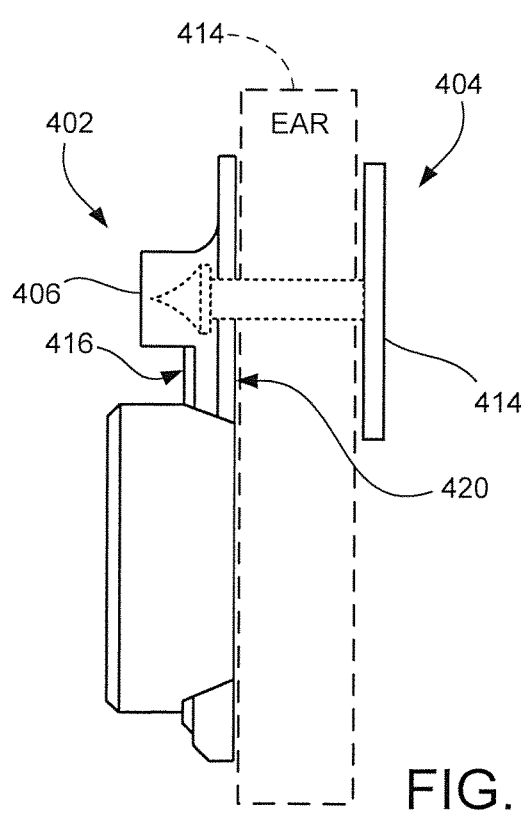
FIG. 26C shows a side elevational representation of the tag assembly in an installed condition.

FIGS. 26A and 26B show respective front and rear views of the tag 402, and FIG. 26C shows a side elevational view of the tag 402 installed using the connector 404. A user indicator device such as an LED display is represented at 416 and can be operated as discussed above to provide a human identifiable visual indicator (e.g., a flashing red light, etc.). A substantially flat back surface 418 is provided to contactingly engage or otherwise be disposed in a facing relation to the ear 114.

As best shown in FIG. 26B, a localized, radiused projection 420 can be provided as desired to extend from the flat back surface 418 toward the ear. The projection 420 houses the primary temperature sensor of the tag 402 and is configured to obtain an accurate outer ear temperature through contact with the outer surface of the ear. As can be seen in FIG. 26C, the projection 420 is located adjacent the aperture 406 so as to be disposed within the radial extent of the base (backing member) 414 of the connection member 404. Other suitable locations for the LED and the temperature sensor can be used as desired.

FIG. 27 corresponds to the rear view of FIG. 26B and shows an exemplary layout for an interior electronic assembly 422 embedded within the tag 402. It is contemplated albeit not necessarily required that the tag 402 is formed using an injection molding process so that an overmold of thermoset plastic or other suitable material 424 encapsulates and seals the interior electronic assembly 422. The overmold material 424 may be thermally insulative or thermally conductive.

The interior electronic assembly 422 is shown in FIG. 28 to include various components including a printed circuit board (PCB) 426, an electrical battery 428, conductive terminals such as 430 to interconnect the battery, and various electronic components including one or more integrated circuit (IC) devices 432, an LED 434 and thermal sensor 436. The thermal sensor 436 operates as the primary or first thermal sensor as discussed above.

The radiused projection 420 from FIG. 26A is shown in greater detail in FIG. 29. It can be seen that the overmold material 424 contactingly encapsulates the assembly 422 and is contoured to obtain the desired shape. The overmold material can be thinned in selected locations such as in the vicinity of the LED 434 and the thermal sensor 436, although depending on the type of overmold material that is used such thinning may not be necessary. As noted above, the use of a radiused projection enhances the thermal coupling of the thermal sensor 426 to the outer ear 114, as well as ensures comfort and promotes hygiene for the animal. Other configurations may be used including a flat contact area for the thermal sensor 436.

From a review of FIGS. 27-29 it can be seen that the center of gravity (COG) for the tag 402 will be below and substantially centered with respect to the aperture 404. This advantageously ensures that the tag 402 will tend to hang in a vertical orientation as shown in FIG. 24. This will tend to ensure that the temperature sensor 436 will remain in or return to an optimal location with respect to the vascular structure of the ear 114 to obtain an accurate outer ear temperature (see e.g., discussion above of FIGS. 8 and 9).

Different connection members may be used to adapt the same tag 402 to different types of animals. FIG. 30A show three different connection members 404A, 404B and 404C. The connection members 404A, 404B and 404C are substantially identical but use different lengths of shafts 410A, 410B and 410C, respectively, for different animals having different sizes and thicknesses of ears (in this case, cattle, bison and goats). In this way, a suitable connection member can be selected and a given tag 402 can be installed. The tag 402 can be easily removed from an animal by cutting the shaft, allowing the tag to be reinstalled on a new animal using a new connection member.

As discussed above, the various embodiments for the tag assemblies disclosed herein provide a number of parametric measurements, including an outer ear temperature of the animal. The outer ear temperature can be obtained, for example, using a shaft-mounted temperature sensor such as shown in FIG. 6A or a surface abutting temperature sensor such as shown in FIG. 29. It has been determined by the inventors that in some cases, outer ear temperature measurements provide useful information regarding the state of an animal that cannot necessarily be gleaned from other temperature measurements, such as a temperature measurement of the main or core body of the animal. Hence, while the tag assemblies disclosed herein can be configured to obtain additional temperature measurements such as a core body temperature measurement using a probe or other sensor that extends into the animal ear canal, such additional measurements are not necessarily required.

Figure 31A:
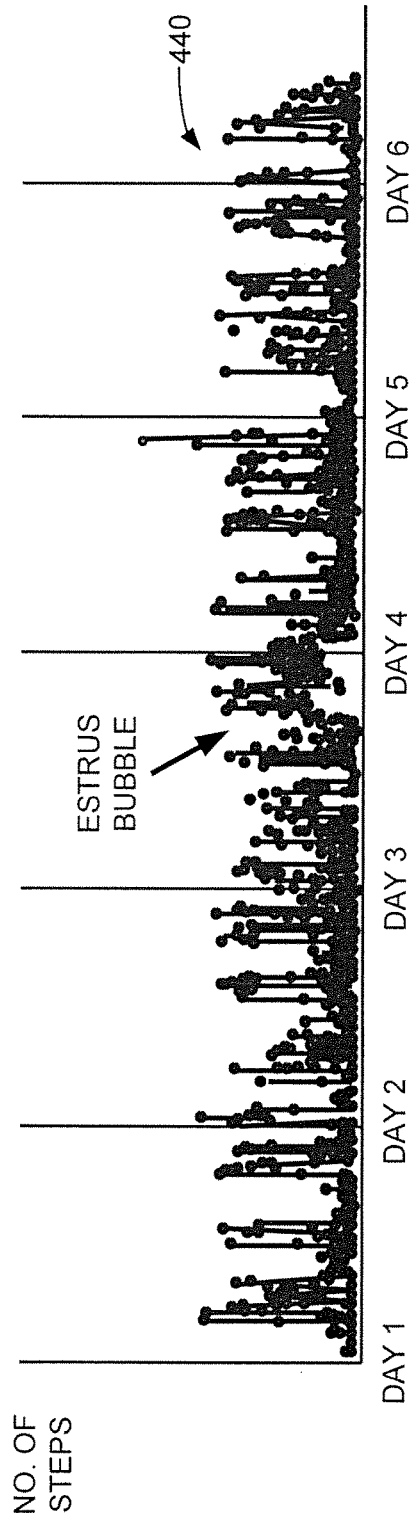
FIGS. 31A and 31B are graphical representations of data obtained from the tag assembly of FIG. 24 useful in detecting a successful insemination of the animal based on the outer ear temperature of the animal in accordance with some embodiments.
Figure 31B:
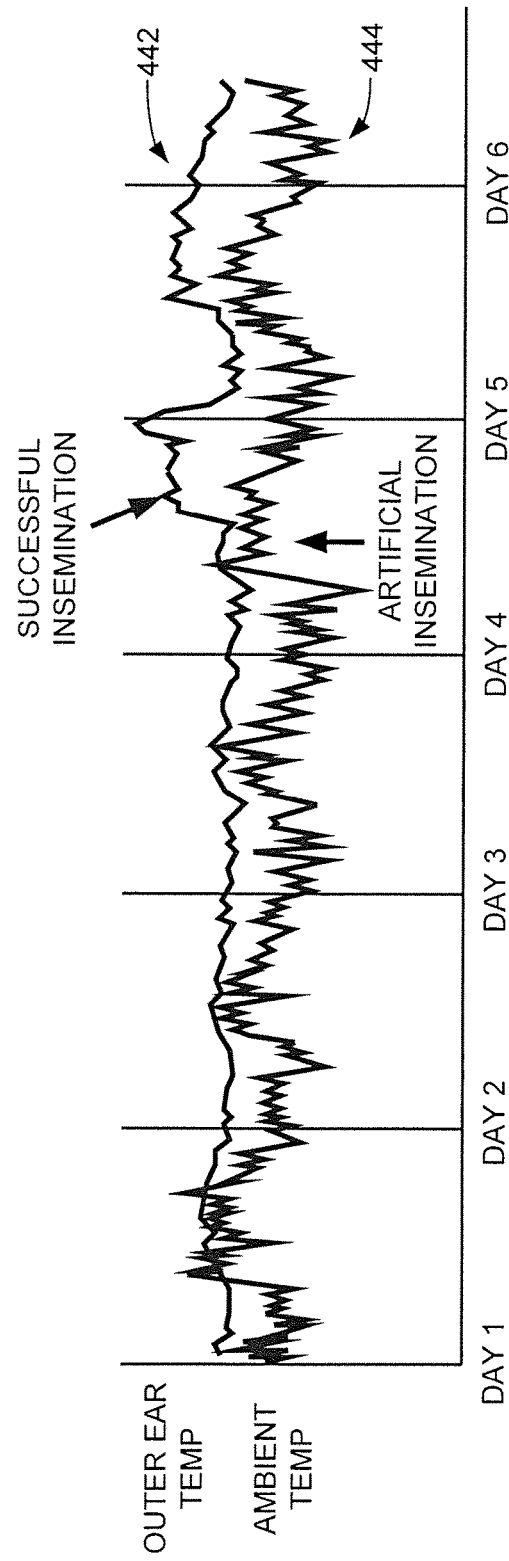

FIGS. 31A and 31B show graphical representations of data obtained using a tag assembly as disclosed herein to detect successful insemination of a cow. As will be recognized by those skilled in the art, successful insemination does not necessarily mean that the animal will undergo a full term pregnancy and birth since there are a number of factors that ultimately determine whether an inseminated animal will keep her new baby. Nevertheless, it is valuable to be able to quickly determine which animals in a herd have been successfully inseminated, enabling the handlers to better understand the optimum conditions for successful breeding.

To this end, FIG. 31A shows activity data 440 indicative of movement of the animal (e.g., number of steps) over a multi-day period. FIG. 31B shows corresponding outer ear temperature data 442 and ambient temperature data 444 for the same animal over the same period of time.

An estrus bubble zone is denoted near the end of Day 3, indicating a higher than normal level of activity that may have been a result of the animal being fertile ("frisky"). An artificial insemination process was applied to the animal during Day 4. The data shows that the outer ear temperature of the animal underwent a subsequent increase in temperature almost immediately after the artificial insemination event. It is theorized that since cows and other large eared animals often use their ears as heat radiators, hormonal changes experienced by the animal as a result of the insemination event caused her ears to heat up, providing near real time feedback that the insemination operation was successful. While artificial insemination was used, it will be appreciated that the same type of data will be exhibited for a natural insemination event involving a male and female animal of the same species behaving in a natural manner.

From these graphs it can be seen that a livestock management system that monitors outer ear temperatures in this manner may be able to enhance the success rate of an insemination program for the herd. Core body temperature excursions may be experienced but can be difficult to detect. Outer ear temperature measurements, on the other hand, can significantly reduce the time required to confirm successful insemination without the need for more intrusive measurements (including vaginal examinations, which can be distressful).

Figure 32A:
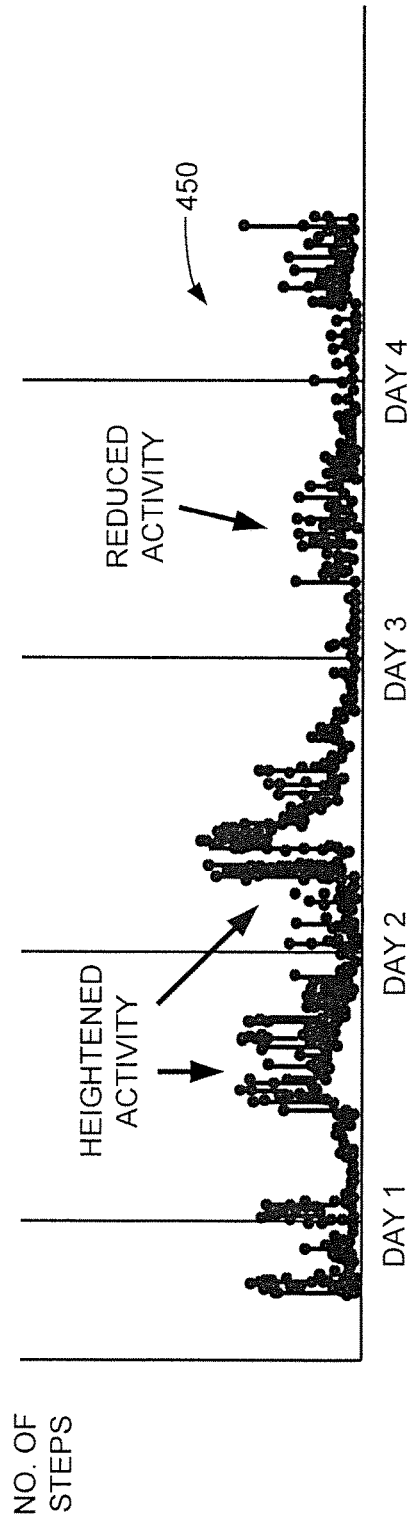
FIGS. 32A and 32B are graphical representations of data obtained from the tag assembly of FIG. 24 useful in detecting an illness of the animal (e.g., milk fever) based on the outer ear temperature of the animal in accordance with some embodiments.
Figure 32B:
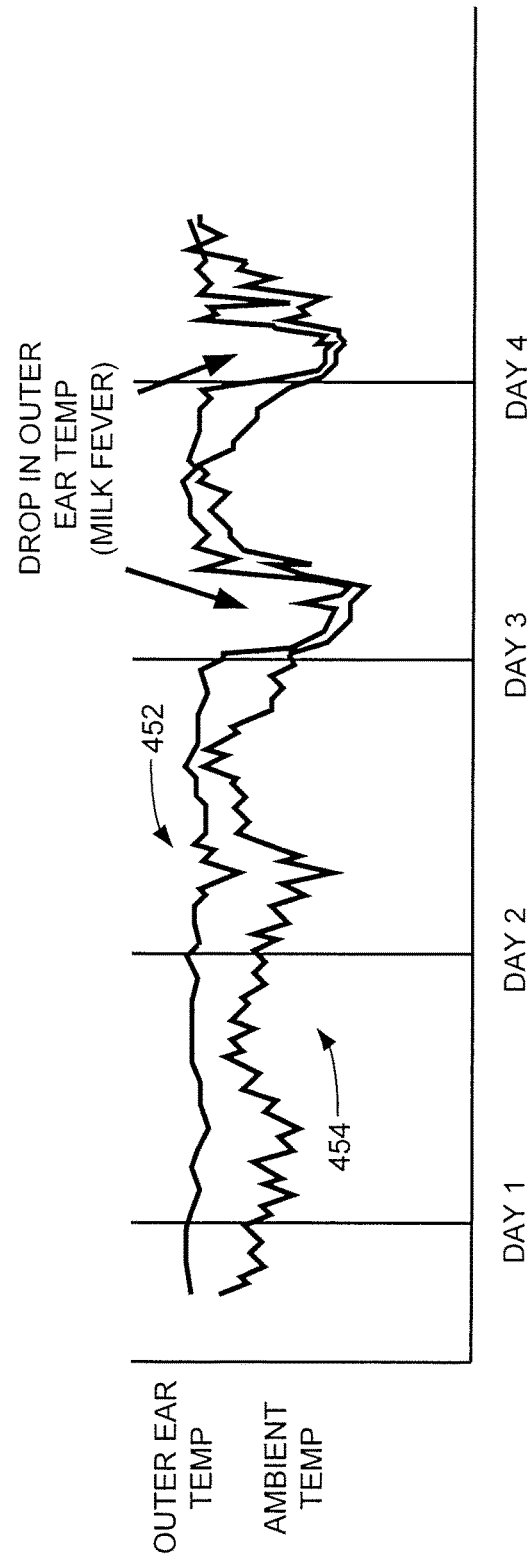

Monitoring outer ear temperature can also facilitate early detection of certain illness conditions associated with an animal, such as depicted in FIGS. 32A and 32B. As before, activity data for a selected animal are represented by curve 450, outer ear temperature is represented at curve 452 and ambient temperature by curve 454.

From the data it can be seen that zones of heightened activity were indicated during Days 1 and 2, while outer ear temperatures remains substantially constant over this period. Beginning on Day 3, however, a significant drop in outer ear temperature occurred, so that the ear temperature largely matched the ambient temperature. In this case, this cooling of the ear temperature signaled that the animal was suffering from postparturient hypocalcemia, or milk fever, commonly associated with a reduction in blood calcium levels. Other states of an animal can readily be determined based on outer ear temperature monitoring, such as heat stress of the animal, etc.

FIG. 33 shows another schematic depiction of a tag assembly 460 similar to the tag assemblies discussed above. In FIG. 33, a primary or first temperature sensor 462 is incorporated into a main body 464 of the tag assembly to obtain outer ear temperatures of an animal. Instead of incorporating the secondary or ambient temperature sensor in the tag, however, an external temperature sensor 466 is provided to obtain the ambient temperature sensor data. The external temperature sensor 466 can be provided at any suitable location, including in or near a data collection unit 468 that wirelessly communicates with the tag assembly when the main body 464 is brought into range (such as adjacent a watering station, milking station, etc.).

At least one additional sensor is shown at 470, and this additional sensor provides additional (other) parametric data for evaluation as well. The sensor 470 may be internal to the tag or may be externally located. As discussed above, any number of parameters can be obtained including a light sensor, activity sensor, methane sensor, humidity sensor, geoposition sensor, etc.

The data collection unit 468 can receive some or all of the data sets in FIG. 33 via one or more wireless data communication links. In some cases, the data collection unit can process the data to provide an indication of a status of the animal through a comparison of the auricle (outer ear) temperature data and the ambient temperature data, alone or in combination with other parametric data. The indication may be provided such as by providing, on a display device, graphical data such as discussed above in FIGS. 16, 31A-31B and 32A-32B. Additionally or alternatively, the indication may be provided using analytical software/firmware, including an expert system that provides user notifications responsive to various detected states. For example, the system can learn to identify successful insemination, milk fever, heat stress, etc. based on these and other combinations of the parametric data. The notifications can be provided using any suitable mechanism, including displayed messages, texts, emails, alerts, etc. as discussed above.

FIG. 34 shows yet another tag assembly 480 in accordance with some embodiments. The tag assembly 480 includes a main body 482 that houses various sensors including a primary temperature sensor 484, a heart rate monitor 486 and a three-axis (XYZ) accelerometer 488. It has been found that an accelerometer 488 can provide useful information such as different types of head movements, such as during rumination (chewing the cud). Generally, a contented cow is more likely to undergo increased rumination as compared to a distressed cow. Other forms of sensors can be used including pulse rate monitors, oxygen saturation sensors, blood flow sensors, etc. that obtain data through optical detection, contact, etc.

FIG. 35 provides a sequence flow diagram 500 illustrative of steps that may be carried out in accordance with some embodiments. Generally, the sequence includes an operation at step 502 to affix a tag assembly to the outer ear of an animal. At step 504, data are periodically transmitted from the tag including outer ear temperature data associated with a surface or shaft measurement of the outer ear. Other data may be transmitted and/or collected during this step as well, such as ambient temperature data and other non-temperature related parameters. At step 506, the collected data are used by a data processing system to determine an existing state of the animal.

FIG. 36 shows the use of an auxiliary sensor 508 which communicates data to an ear tag 510. The auxiliary sensor 508 is a physically separate sensor that is attached to or otherwise disposed proximate the animal. Examples include sensors that attach to an external portion of the animal body (e.g., a leg, a tail, etc.), sensors that are ingested (e.g., swallowed), and so on. These specially configured sensors may be configured to transmit parametric data using a short range wireless communication protocol. The transmitted data are detected, stored and forwarded by the tag 510 to the base unit 512. The transmitted data from the tag 510 to the base unit 512 include data accumulated by the auxiliary sensor 508 as well as data accumulated by various sensors of the tag 510.

Any number of wireless communication protocols may be used as required to communicate data between the various operative elements of the system. Without limitation, these can include RFID, NEC, Bluetooth, Wi-FI, ZigBee, cellular, server specific protocols, etc. Conformance can be made with various industry established communication standards including but not limited to ISO 18000, ISO 14443, IEEE 802.11, IEEE 802.15, the Blouetooth Special Interest Group (SIG), etc. The same communication protocol can be used throughout the system or different protocols can be used to handle communications between individual pairs of devices as required (see e.g., FIG. 1).

Figure 37:
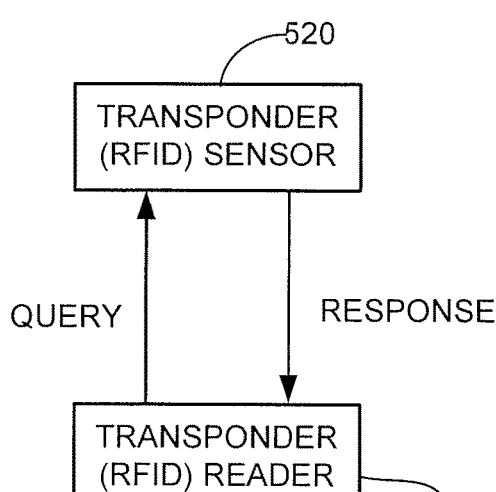
FIG. 37 shows a general communication sequence between wireless transponders in the form of a sensor and a reader in accordance with some embodiments.

FIG. 37 is a simplified functional diagram showing the wireless communication interaction between a transponder sensor 520 and a transponder reader 522. The sensor 520, also referred to as a radio frequency identification (RFID) tag or an RFID sensor, is a wireless circuit configured to receive interrogation (query) signals from the reader 522, also referred to as an RFID reader circuit. In response to the query signals, the sensor 520 operates to transmit a response signal. The response signal emitted by the sensor will include a tag identification (ID) value that uniquely identifies the tag. Depending on the configuration of the tag, the response signal may include additional information as well.

Figure 38:
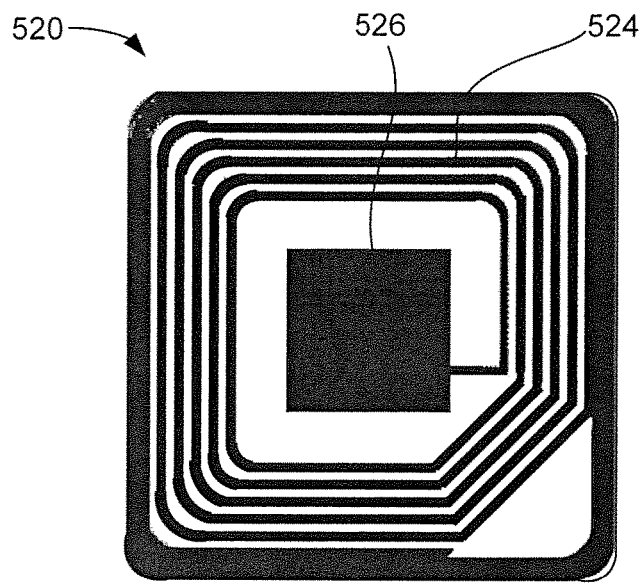
FIG. 38 is a schematic depiction of the sensor in FIG. 37 in some embodiments.

FIG. 38 shows one example configuration for the RFID sensor 520. The sensor generally has an antenna 524 and a processing circuit 526. The processing circuit 526 includes the necessary active or passive circuit elements to enable the antenna 524 to receive and broadcast wireless information signals with the reader 522. The antenna may include a waveguide or other circuit path arranged in an EMF (electromagnetic frequency) responsive configuration, as generally depicted in FIG. 38.

Sensors 520 can come in a variety of forms including passive and active. Passive sensors do not include an integrated power source, but instead are activated by EMF energy supplied via activation of the antenna. Active sensors may include or otherwise use a separate power source, such as an integrated battery or a battery used to power other circuitry associated with but separate from the sensor. Sensors can further be configured to be writeable, rewritable, etc. so that a reader such as 522 can write data to the sensor 520 during a wireless communication session.

Figure 39:
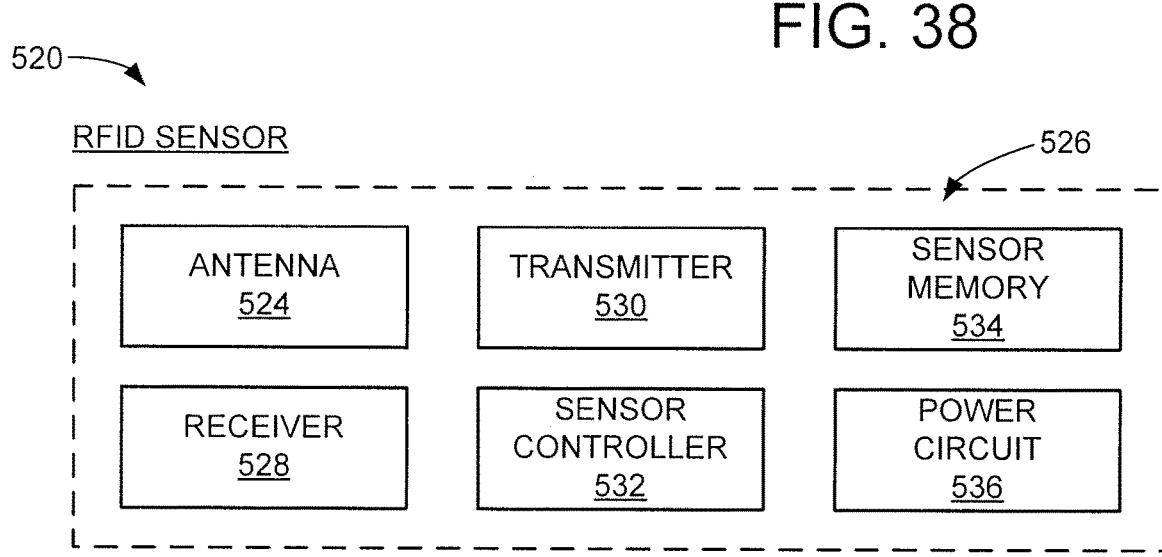
FIG. 39 is a functional block representation of the sensor of FIG. 37 in some embodiments.

An active writeable configuration for the RFID sensor 520 is denoted in FIG. 39. Other configurations can be used including non-writeable sensors, passive sensors, etc. The processing circuit 526 of the RFID sensor 520 includes a receiver 528, a transmitter 530, a reader controller 532, reader memory 534 and a power circuit 536. These constituent elements are configured to enable the reader 522 to activate the sensor 520, retrieve information therefrom including the unique sensor ID value, and write one or more data values to the sensor memory 534.

Figure 40:
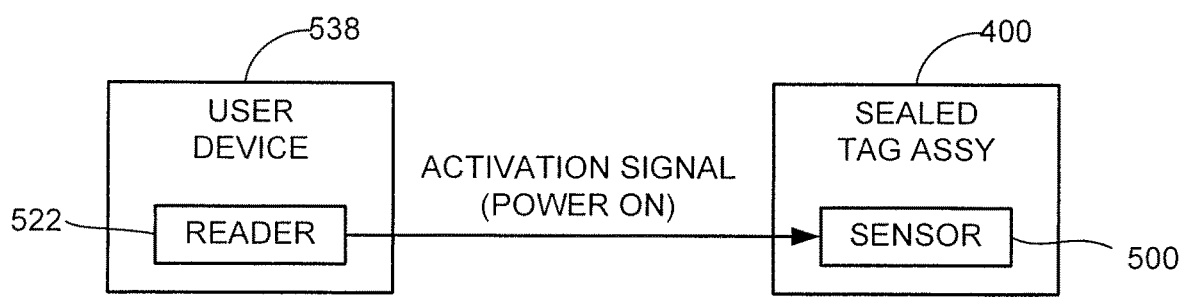
FIG. 40 illustrates a wireless activation operation with a selected tag assembly using the elements of FIGS. 37-39 in accordance with some embodiments.

This configuration enables the various tags in the system, such as but limited to the sealed tag assembly 400 from FIGS. 24-29, to be remotely activated during installation. As depicted in FIG. 40, once the tag assembly 400 has been installed onto the animal 114 (see FIG. 24), a reader such as 522 in a user device 538 can provide an activation signal to the sensor 520 within the tag assembly 400. This can result in the writing of a suitable value or instruction to the sensor memory 534, which in turn is used by the sensor controller 532 to activate the rest of the tag 400, including energizing the main battery 428 and bringing the main controller circuitry (e.g., IC devices 432) online.

In this way, manufactured tags can be hermetically sealed against the external environment and will remain essentially inert until ready for use so that little or no main battery power is drained prior to installation. The tags 400 can be conveniently placed into operational service upon installation by bringing the user device 538 into proximity with the tag and activating the tag wirelessly. This configuration eliminates the need for a separate on/off switch, an insulative pull tab that is removed to allow contact between the battery 428 and the electrical contact 430, etc.

It will now be appreciated that the various embodiments presented herein have a number of advantages and benefits over the existing art. The use of multiple temperature sensors help to correlate changes in the state of the animal, particularly when combined with other sensors that provide a better indication of ambient conditions. Heat stress and other conditions can be more accurately assessed and compensated. The tag data can be collected and transferred in a variety of ways and analyzed to further livestock management efforts in a wide variety of areas.

While the various embodiments have been described in terms of domesticated livestock animals, particularly cattle, the embodiments can be readily adapted for any number of other applications including being used with substantially any form of animal, including domesticated or wild mammals, humans, etc.

It is to be understood that even though numerous characteristics and advantages of various embodiments of the present disclosure have been set forth in the foregoing description, this description is illustrative only, and changes may be made in detail, especially in matters of structure and arrangements of parts within the principles of the present disclosure to the full extent indicated by the broad general meaning of the terms wherein the appended claims are expressed.

What is claimed is:

1. An apparatus comprising:
a tag assembly configured for attachment to an outer ear of an animal, the tag assembly comprising a main body and a shaft that extends through an aperture extending through the outer ear to attach the main body to a facing surface of the outer ear, the tag assembly further comprising a primary temperature sensor configured to obtain outer ear temperature data indicative of an outer ear temperature of the outer ear; and
a control circuit configured to receive the outer ear temperature data via a wireless communication link with the tag assembly and to determine a health state of the animal responsive to a difference between a magnitude of the outer ear temperature data and a magnitude of a set of ambient temperature data obtained from an ambient temperature sensor proximate the animal over a selected time interval, the localized change in the magnitude of the outer temperature data not adjusted using the set of ambient temperature data or a set of core temperature data obtained from a core temperature sensor that measures an internal temperature of the animal.

2. The apparatus of claim 1, wherein the ambient temperature sensor is incorporated into the tag assembly.

3. The apparatus of claim 1, wherein the ambient temperature sensor comprises a separate sensor that communicates the ambient temperature data to the tag assembly using a second wireless communication link, and wherein the tag assembly further communicates the ambient temperature data to the control circuit using the wireless communication link.

4. The apparatus of claim 1, further comprising a secondary sensor configured to obtain secondary sensor data associated with the animal, wherein the control circuit further operates to determine the health state of the animal responsive to the secondary sensor data.

5. The apparatus of claim 1, wherein the health state of the animal is determined responsive to the magnitude of the outer ear temperature data dropping to a level nominally equal to a magnitude of the ambient temperature data, and wherein the health state is determined independently of any other temperature measurement associated with the animal.

6. The apparatus of claim 1, wherein the health state of the animal is determined responsive to the magnitude of the outer ear temperature data exceeding a magnitude of the ambient temperature data by a selected temperature interval.

7. The apparatus of claim 1, wherein the primary temperature sensor is incorporated into the main body of the tag assembly and pressingly engages the facing surface of the outer ear.

8. The apparatus of claim 1, wherein the tag assembly further comprises an additional sensor that provides additional parametric data that is transmitted via the wireless communication link to the control circuit, wherein the additional sensor is a selected one of an activity monitor, a geoposition sensor, an optical sensor, a humidity sensor, a light sensor, a methane sensor, a proximity sensor, a heart rate monitor, a pulse rate monitor, an oxygen saturation monitor, a blood flow sensor, a core body temperature sensor, or a multi-axis accelerometer.

9. The apparatus of claim 1, further comprising an auxiliary sensor configured to be located proximate the animal at a separate location apart from the tag assembly, the auxiliary sensor configured to transmit auxiliary parametric data to the tag assembly, the tag assembly further configured to transmit the auxiliary parametric data to the control circuit via the wireless communication link.

10. The apparatus of claim 1, wherein the shaft has a proximal end that is permanently affixed to the backing member and a pointed distal end configured to pierce the outer ear of the animal and engage an aperture in the main body, the tag assembly further comprising a backing member configured to contactingly engage the pointed distal end of the shaft to connect the tag assembly to the outer ear.

11. The apparatus of claim 1, wherein the control circuit generates and transmits, to a user device, a notification of the health state of the animal responsive to a change in relative temperature differences between the outer ear temperature data and the ambient temperature data, the detected state comprising a selected one of heat stress, illness or successful insemination.

12. The apparatus of claim 1, wherein the tag assembly further comprises an RFID (radio frequency identification) transponder to communicate with the control circuit.

13. A system for monitoring a health status of an animal, comprising:
a tag assembly configured for attachment to an outer ear of an animal, the tag assembly comprising a primary temperature sensor and at least one auxiliary sensor, the primary temperature sensor configured to obtain outer ear temperature data indicative of an outer ear temperature of the outer ear, the at least one auxiliary sensor configured to obtain parametric data associated with the animal;
a control circuit configured to receive the outer ear temperature data and the parametric data via a first wireless communication link with the tag assembly responsive to a detection, by the control circuit, of an RFID (radio frequency identification) transponder signal broadcast by the tag assembly, the control circuit configured to determine a health state of the animal responsive to a change in magnitude over time of the outer ear temperature data and to transmit the health state, via a second wireless communication link, to a user device, wherein neither the tag assembly or the control circuit calculates an adjusted temperature for the outer ear temperature prior to determining the health state of the animal.

14. The system of claim 13, further comprising an external sensor in a selected stationary location configured to obtain second parametric data associated with the animal, the external sensor transmitting the second parametric data to the tag assembly which, in turn, transmits the second parametric data to the control circuit via the first wireless communication link.

15. The system of claim 13, wherein the control circuit determines the health state of the animal responsive to a localized change in a magnitude of the outer ear temperature data in relation to a magnitude of a set of ambient temperature data obtained from an ambient temperature sensor proximate the animal over a selected time interval.

16. The system of claim 13, wherein the health state of the animal is determined responsive to the magnitude of the outer ear temperature data dropping to a level nominally equal to a magnitude of the ambient temperature data.

17. The system of claim 13, wherein the health state of the animal is determined responsive to the magnitude of the outer ear temperature data exceeding a magnitude of the ambient temperature data by a selected temperature interval.

18. The system of claim 13, wherein the control circuit is further configured to transmit, via the first wireless network, an activation signal to energize a power source of the tag assembly to transition the tag assembly from a deactivated state to an activated state after installation of the tag assembly onto the animal.

19. The system of claim 13, wherein the animal is a cow.

20. An apparatus comprising:
a tag assembly configured for attachment to an outer ear of an animal, the tag assembly comprising a main body and a shaft that extends through an aperture extending through the outer ear to attach the main body to a facing surface of the outer ear, the tag assembly further comprising a primary temperature sensor configured to obtain outer ear temperature data indicative of an outer ear temperature of the outer ear; and
a control circuit configured to receive the outer ear temperature data via a first wireless communication link with the tag assembly and to determine a health state of the animal responsive to a localized change in a magnitude of the outer ear temperature data in relation to a magnitude of a set of ambient temperature data obtained from an ambient temperature sensor proximate the animal over a selected time interval, wherein the ambient temperature sensor comprises a separate sensor that communicates the ambient temperature data to the tag assembly using a second wireless communication link, and wherein the tag assembly further communicates the ambient temperature data to the control circuit using the first wireless communication link.

* * * * *